US012365853B2

(12) United States Patent
Herrmann et al.

(10) Patent No.: US 12,365,853 B2
(45) Date of Patent: Jul. 22, 2025

(54) CLEAVABLE MULTI-ALCOHOL-BASED MICROCAPSULES

(71) Applicant: FIRMENICH SA, Satigny (CH)

(72) Inventors: Andreas Herrmann, Satigny (CH); Damien Berthier, Satigny (CH); Serge Lamboley, Satigny (CH); Kitty Van Gruijthuijsen, Satigny (CH); Nicolas Paret, Satigny (CH)

(73) Assignee: FIRMENICH SA, Satigny (CH)

( * ) Notice: Subject to any disclaimer, the term of this patent is extended or adjusted under 35 U.S.C. 154(b) by 942 days.

(21) Appl. No.: 17/437,870

(22) PCT Filed: Jul. 31, 2020

(86) PCT No.: PCT/EP2020/071627
§ 371 (c)(1),
(2) Date: Sep. 10, 2021

(87) PCT Pub. No.: WO2021/023645
PCT Pub. Date: Feb. 11, 2021

(65) Prior Publication Data
US 2022/0169954 A1 Jun. 2, 2022
US 2023/0250369 A9 Aug. 10, 2023

(30) Foreign Application Priority Data

Aug. 5, 2019 (EP) .................................... 19190061

(51) Int. Cl.
*C11D 3/37* (2006.01)
*A01N 25/28* (2006.01)
(Continued)

(52) U.S. Cl.
CPC ............... *C11D 3/505* (2013.01); *B01J 13/16* (2013.01); *C11D 3/2041* (2013.01); *C11D 3/2065* (2013.01)

(58) Field of Classification Search
CPC ....... C11D 3/2041; C11D 3/2065; C11D 3/37; C11D 3/50; C11D 3/505; C11D 11/00;
(Continued)

(56) References Cited

U.S. PATENT DOCUMENTS 11,291,969 B2 * 4/2022 Ouali ....................... A61K 8/85
2018/0078468 A1 3/2018 Jerri et al.

FOREIGN PATENT DOCUMENTS

CN 108472616 A 8/2018
EP 2999457 A1 3/2016
(Continued)

OTHER PUBLICATIONS

International Search Report and Written Opinion for corresponding PCT/EP2020/071627 mailed Oct. 14, 2020, 13 pages.

*Primary Examiner* — Brian P Mruk
(74) *Attorney, Agent, or Firm* — Armstrong Teasdale LLP

(57) ABSTRACT

Described herein is a process for a preparation of microcapsules based on cleavable multi-alcohols. Also described herein are cleavable multi-alcohol-based microcapsules. Also described herein are perfuming compositions and consumer products including such capsules, in particular perfumed consumer products in the form of home care or personal care products.

11 Claims, 1 Drawing Sheet

(51) Int. Cl.
*A61K 8/11* (2006.01)
*B01J 13/16* (2006.01)
*C11D 3/20* (2006.01)
*C11D 3/50* (2006.01)
*C11D 11/00* (2006.01)

(58) Field of Classification Search
CPC ........ C11D 11/0064; A61K 8/11; B01J 13/16; A01N 25/28
See application file for complete search history.

(56) References Cited

FOREIGN PATENT DOCUMENTS

| WO | 0119509 A1 | 3/2001 | | |
|---|---|---|---|---|
| WO | 2007004166 A1 | 1/2007 | | |
| WO | 2018054719 A1 | 3/2018 | | |
| WO | 2019002380 A1 | 1/2019 | | |
| WO | WO 2019/002380 | * | 1/2019 | .............. B01J 13/16 |
| WO | WO-2019121738 A1 | * | 6/2019 | ................ A61K 8/11 |

* cited by examiner

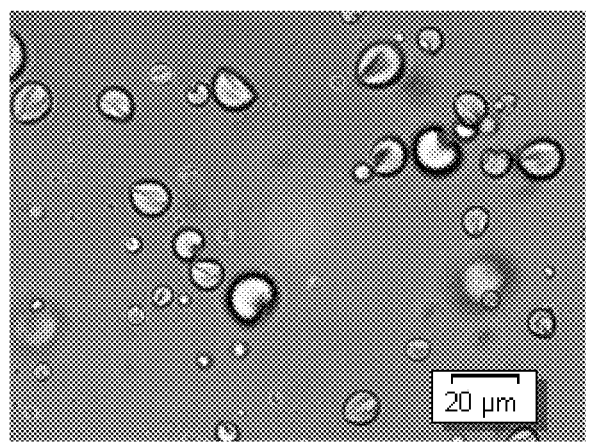

CLEAVABLE MULTI-ALCOHOL-BASED MICROCAPSULES

CROSS-REFERENCE TO RELATED APPLICATIONS

This application is a U.S. National Phase Application of International Patent Application No. PCT/EP2020/071627, filed Jul. 31, 2020, which claims priority to European Patent Application Ser. No. 19/190,061.2 filed Aug. 5, 2019, the entire contents of which are hereby incorporated by reference herein.

TECHNICAL FIELD

The present invention relates to a new process for the preparation of microcapsules based on cleavable multi-alcohols. Cleavable multi-alcohol-based microcapsules are also an object of the invention. Perfuming compositions and consumer products comprising said capsules, in particular perfumed consumer products in the form of home care or personal care products, are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume are needed to protect and later release the core payload when triggered. A key requirement from the industry regarding these systems is to survive suspension in challenging bases without physically dissociating or degrading. This is referred to as stability for the delivery system. For instance, fragranced personal and household cleansers containing high levels of aggressive surfactant detergents are very challenging for the stability of microcapsules.

Polyurea and polyurethane-based microcapsule slurries are widely used in the perfumery industry for instance as they provide a long lasting pleasant olfactory effect after their applications on different substrates. Those microcapsules have been widely disclosed in the prior art (see for example WO2007/004166 or EP 2300146 from the Applicant).

There is still a need to provide new microcapsules, while not compromising on the performance of the capsules, in particular in terms of stability in a challenging medium such as a consumer product base, as well as in delivering a good performance in terms of active ingredient delivery, e.g. olfactive performance in the case of perfuming ingredients.

The present invention is proposing a solution to the above-mentioned problem, by providing new microcapsules based on cleavable multi-alcohols using covalent adaptable networks based on reversible reactions.

SUMMARY OF THE INVENTION

It has now surprisingly been found that performing core-shell microcapsules encapsulating hydrophobic ingredients could be obtained by using cleavable multi-alcohols as building blocks for preparing the polymeric wall of the microcapsules. It has been shown that the presence of covalent adaptable networks can provide performing microcapsules.

The process of the invention therefore provides a solution to the above-mentioned problems as it allows preparing microcapsules with the desired stability in challenging bases.

In a first aspect, the present invention relates to a process for the preparation of a core-shell microcapsule slurry comprising the following steps:
a) adding at least one polyfunctional monomer in a hydrophobic material, preferably a perfume, to form an oil phase;
b) preparing a dispersing phase, wherein the dispersing phase is not miscible with the oil phase;
c) adding the oil phase into the dispersing phase to form a two-phase dispersion;
d) optionally, adding a reactant to the dispersion obtained in step c); and
e) performing a curing step to form core-shell microcapsules in the form of a slurry, wherein a stabilizer is added in step a) and/or step b), and
wherein at least one cleavable multi-alcohol is added in step a) and/or in step b) and/or in step c) and/or in step d),
wherein the cleavable multi-alcohol has the following formula (I)

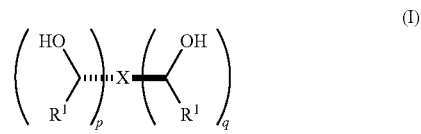

wherein each $R^1$ is independently H or $CH_2OH$ and wherein p and q are integers varying between 1 and 3, preferably p and q are either 1 or 2, and
wherein X is a $C_2$ to $C_{30}$ hydrocarbon group, possibly comprising one to ten heteroatoms, selected from O, S and N to form ether, ester, carboxylic acid, aldehyde, ketone, alcohol, thiol, disulfide, thioether, thioester, carbamate, amide, oxime, imine, amine or nitrile functional groups.

In a second aspect, the present invention relates to a core-shell microcapsule comprising:
an oil-based core comprising a hydrophobic material, preferably a perfume, and
a shell comprising a reaction product between a polyfunctional monomer and a cleavable multi-alcohol as defined above.

A third object of the invention is a core-shell microcapsule slurry comprising at least one microcapsule having:
an oil-based core comprising a hydrophobic material, preferably a perfume, and
a shell comprising a reaction product between a polyfunctional monomer and a cleavable multi-alcohol as defined above.

A fourth object of the invention is a core-shell microcapsule slurry obtainable by the process as defined above.

A perfuming composition comprising:
(i) microcapsules or a microcapsule slurry as defined above, wherein the hydrophobic material comprises a perfume,
(ii) at least one ingredient selected from the group consisting of a perfumery carrier and a perfumery base,
(iii) optionally at least one perfumery adjuvant,
is another object of the invention.

Another object of the invention is a consumer product comprising:
- a personal care active base, and
- microcapsules or microcapsule slurry as defined above or the perfuming composition as defined above,
- wherein the consumer product is in the form of a personal care composition.

Another object of the invention is a consumer product comprising:
- a home care or a fabric care active base, and
- microcapsules or microcapsule slurry as defined above or the perfuming composition as defined above,
- wherein the consumer product is in the form of a home care or a fabric care composition.

DETAILED DESCRIPTION OF THE INVENTION

Unless stated otherwise, percentages (%) are meant to designate a percentage by weight of a composition.

By "active ingredient", it is meant a single compound or a combination of ingredients.

By "perfume or flavor oil", it is meant a single perfuming or flavoring compound or a mixture of several perfuming or flavoring compounds.

By "consumer product" or "end-product" it is meant a manufactured product ready to be distributed, sold and used by a consumer.

For the sake of clarity, by the expression "dispersion" in the present invention it is meant a system in which particles are dispersed in a continuous phase of a different composition and it specifically includes a suspension or an emulsion.

A "microcapsule", or the similar, in the present invention it is meant that core-shell microcapsules have a particle size distribution in the micron range (e.g. a mean diameter (d(v, 0.5)) comprised between about 1 and 3000 microns, preferably comprised between 1 and 1000 microns, more preferably between 1 and 500 microns, and even more preferably between 5 and 50 microns) and comprise an external solid polymer-based shell and an internal continuous oil phase enclosed by the external shell.

By "microcapsule slurry", it is meant microcapsule(s) that is (are) dispersed in a liquid.

According to an embodiment, the slurry is an aqueous slurry, i.e the microcapsule(s) is (are) dispersed in an aqueous phase.

By "polyfunctional monomer", it is meant a molecule that, as unit, reacts or binds chemically to form a polymer or a supramolecular polymer. The polyfunctional monomer of the invention has at least two functional groups that are capable to react with or bind to functional groups of another monomer to form a (polymeric) microcapsule shell. The wording "shell" and "wall" are used indifferently in the present invention.

By "cleavable multi-alcohol", it is meant a multiol or a polyol having the following formula

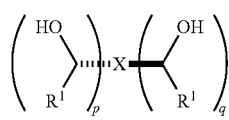

(I)

wherein each $R^1$ is independently H or $CH_2OH$ and wherein p and q are integers varying between 1 and 3, preferably p and q are either 1 or 2, and wherein X is a $C_2$ to $C_{30}$ hydrocarbon group, possibly comprising one to ten heteroatoms, selected from O, S and N to form ether, ester, carboxylic acid, aldehyde, ketone, alcohol, thiol, disulfide, thioether, thioester, carbamate, amide, oxime, imine, amine or nitrile functional groups.

According to the invention, X can be split into at least two separate pieces by the cleavage of one or several covalent bonds as the consequence of a redox-reaction, hydrolysis, a retro-1,4-addition, the action of light and/or combinations thereof.

According to the invention "poly acid chloride" and "poly acyl chloride" are used indifferently.

It has been found that core-shell microcapsules with overall good performance in challenging bases could be obtained by reacting a cleavable multi-alcohol with at least one other polyfunctional monomer during the process of forming a polymeric capsule shell. These cleavable multi-alcohols were surprisingly stable in challenging bases when present in the shell as a co-monomer.

FIGURES

FIG. 1 represents an optical micrograph picture of poly (urethane) core-shell microcapsules according to the invention.

PROCESS FOR PREPARING A MICROCAPSULE SLURRY

A first object of the invention is a process for the preparation of a core-shell microcapsule slurry comprising the following steps:
- a) adding at least one polyfunctional monomer in a hydrophobic material, preferably a perfume, to form an oil phase;
- b) preparing a dispersing phase, wherein the dispersing phase is not miscible with the oil phase;
- c) adding the oil phase into the dispersing phase to form a two-phase dispersion;
- d) optionally, adding a reactant to the dispersion obtained in step c); and
- e) performing a curing step to form core-shell microcapsules in the form of a slurry,
  wherein a stabilizer is added in step a) and/or step b), and
  wherein at least one cleavable multi-alcohol is added in step a) and/or in step b) and/or in step c) and/or in step d),
  wherein the cleavable multi-alcohol has the following formula (I)

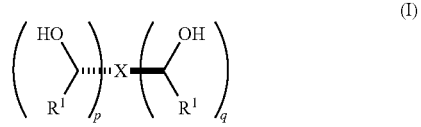

(I)

wherein each $R^1$ is independently H or $CH_2OH$ and wherein p and q are integers varying between 1 and 3, preferably p and q are either 1 or 2, and wherein X is a $C_2$ to $C_{30}$ hydrocarbon group, possibly comprising one to ten heteroatoms, selected from O, S and N to form ether, ester, carboxylic acid, aldehyde, ketone, alcohol, thiol, disulfide, thioether, thioester, carbamate, amide, oxime, imine, amine or nitrile functional groups.

Step a): Adding at Least One Polyfunctional Monomer in a Hydrophobic Material, Preferably a Perfume, to Form an Oil Phase Hydrophobic Material The hydrophobic material according to the invention can be an "inert" material like solvents or active ingredients.

When hydrophobic materials are active ingredients, they are preferably chosen from the group consisting of flavors, flavor ingredients, perfumes, perfume ingredients, nutraceuticals, cosmetics, pest control agents, biocide actives and mixtures thereof.

According to a particular embodiment, the hydrophobic material comprises a mixture of a perfume with another ingredient selected from the group consisting of nutraceuticals, cosmetics, pest control agents and biocide actives.

According to a particular embodiment, the hydrophobic material comprises a mixture of biocide actives with another ingredient selected from the group consisting of perfumes, nutraceuticals, cosmetics, pest control agents.

According to a particular embodiment, the hydrophobic material comprises a mixture of pest control agents with another ingredient selected from the group consisting of perfumes, nutraceuticals, cosmetics, biocide actives.

According to a particular embodiment, the hydrophobic material comprises a perfume.

According to a particular embodiment, the hydrophobic material consists of a perfume.

According to a particular embodiment, the hydrophobic material consists of biocide actives.

According to a particular embodiment, the hydrophobic material consists of pest control agents.

By "perfume" (or also "perfume oil") what is meant here is an ingredient or a composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odor. In other words, such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes a combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lastingness, blooming, malodor counteraction, antimicrobial effect, microbial stability, pest control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said ingredients may also be compounds known to release in a controlled manner various types of perfuming compounds also known as properfume or profragrance. Non-limiting examples of suitable properfumes may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-phenylethyl oxo(phenyl)acetate, 3,7-dimethylocta-2,6-dien-1-yl oxo(phenyl)acetate, (Z)-hex-3-en-1-yl oxo(phenyl)acetate, 3,7-dimethyl-2,6-octadien-1-yl hexadecanoate, bis(3,7-dimethylocta-2,6-dien-1-yl)succinate, (2-((2-methylundec-1-en-1-yl)oxy)ethyl)benzene, 1-methoxy-4-(3-methyl-4-phenethoxybut-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en-2-yl)benzene, 2-(1-phenethoxyprop-1-en-2-yl)naphthalene, (2-phenethoxyvinyl)benzene, 2-(1-((3,7-dimethyloct-6-en-1-yl)oxy)prop-1-en-2-yl)naphthalene or a mixture thereof.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Preferred perfuming ingredients are those having a high steric hindrance and in particular those from one of the following groups:

Group 1: perfuming ingredients comprising a cyclohexane, cyclohexene, cyclohexanone or cyclohexenone ring substituted with at least one linear or branched $C_1$ to $C_4$ alkyl or alkenyl substituent;

Group 2: perfuming ingredients comprising a cyclopentane, cyclopentene, cyclopentanone or cyclopentenone ring substituted with at least one linear or branched $C_4$ to $C_8$ alkyl or alkenyl substituent;

Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;

Group 4: perfuming ingredients comprising at least two fused or linked $C_5$ and/or $C_6$ rings;

Group 5: perfuming ingredients comprising a camphor-like ring structure;

Group 6: perfuming ingredients comprising at least one $C_7$ to $C_{20}$ ring structure;

Group 7: perfuming ingredients having a log P value above 3.5 and comprising at least one tert-butyl or at least one trichloromethyl substituent;

Examples of ingredients from each of these groups are:

Group 1: 2,4-dimethyl-3-cyclohexene-1-carbaldehyde (origin: Firmenich SA, Geneva, Switzerland), isocyclocitral, menthone, isomenthone, methyl 2,2-dimethyl-6-methylene-1-cyclohexanecarboxylate (origin: Firmenich SA, Geneva, Switzerland), nerone, terpineol, dihydroterpineol, terpenyl acetate, dihydroterpenyl acetate, dipentene, eucalyptol, hexylate, rose oxide, (S)-1,8-p-menthadiene-7-ol (origin: Firmenich SA, Geneva, Switzerland), 1-p-menthene-4-ol, (1RS,3RS,4SR)-3-p-mentanyl acetate, (1R,2S,4R)-4,6,6-trimethyl-bicyclo[3,1,1]heptan-2-ol, tetrahydro-4-methyl-2-phenyl-2H-pyran (origin: Firmenich SA, Geneva, Switzerland), cyclohexyl acetate, cyclanol acetate, 1,4-cyclohexane diethyldicarboxylate (origin: Firmenich SA, Geneva, Switzerland), (3ARS,6SR,7ASR)-perhydro-3,6-dimethyl-benzo[B]furan-2-one (origin: Firmenich SA, Geneva, Switzerland), ((6R)-perhydro-3,6-dimethyl-benzo[B]furan-2-one (origin: Firmenich SA, Geneva, Switzerland), 2,4,6-trimethyl-4-phenyl-1,3-dioxane, 2,4,6-trimethyl-3-cyclohexene-1-carbaldehyde;

Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3'-cyclopenten-1'-yl)-2-buten-1-ol (origin: Firmenich SA, Geneva, Switzerland), (1'R,E)-3,3-dimethyl-5-(2',2',3'-trimethyl-3'-cyclopenten-1'-yl)-4-penten-2-ol (origin: Firmenich SA, Geneva, Switzerland), 2-heptylcyclopentanone, methyl-cis-3-oxo-2-pentyl-1-cyclopentane acetate (origin: Firmenich SA, Geneva, Switzerland), 2,2,5-Trimethyl-5-pentyl-1-cyclopentanone (origin: Firmenich SA, Geneva, Switzerland), 3,3-dimethyl-5-(2,2,3-trimethyl-3-cyclopenten-1-yl)-4-penten-2-ol (origin: Firmenich SA, Geneva, Switzerland), 3-methyl-5-(2,2,3-trimethyl-3-cyclopenten-1-yl)-2-pentanol (origin, Givaudan SA, Vernier, Switzerland);

Group 3: damascones, 1-(5,5-dimethyl-1-cyclohexen-1-yl)-4-penten-1-one (origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, mixture of 1-(5,5-dimethyl-1-cyclohexen-1-yl)-4-penten-1-one and 1-(3,3-dimethyl-1-cyclohexen-1-yl)-4-penten-1-one (origin: Firmenich SA, Geneva, Switzerland), 1-(2,6,6-trimethyl-1-cyclohexen-1-yl)-2-buten-1-one (origin: Firmenich SA, Geneva, Switzerland), (1S,1'R)-[1-(3',3'-Dimethyl-1'-cyclohexyl)ethoxycarbonyl]methyl propanoate (origin: Firmenich SA, Geneva, Switzerland), 2-tert-butyl-1-cyclohexyl acetate (origin: International Flavors and Fragrances, USA), 1-(2,2,3,6-tetramethyl-cyclohexyl)-3-hexanol (origin: Firmenich SA, Geneva, Switzerland), trans-1-(2,2,6-trimethyl-1-cyclohexyl)-3-hexanol (origin: Firmenich SA, Geneva, Switzerland), (E)-3-methyl-4-(2,6,6-trimethyl-2-cyclohexen-1-yl)-3-buten-2-one, terpenyl isobutyrate, 4-(1,1-dimethylethyl)-1-cyclohexyl acetate (origin: Firmenich SA, Geneva, Switzerland), 8-methoxy-1-p-menthene, (1S,1'R)-2-[1-(3',3'-dimethyl-1'-cyclohexyl)ethoxy]-2-methylpropyl propanoate (origin: Firmenich SA, Geneva, Switzerland), para tert-butylcyclohexanone, menthenethiol, 1-methyl-4-(4-methyl-3-pentenyl)-3-cyclohexene-1-carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), a mixture of (1RS,2SR,6RS,7RS,8SR)-tricyclo[5.2.1.0~2,6~]dec-3-en-8-yl 2-methylpropanoate and (1RS,2SR,6RS,7RS,8SR)-tricyclo[5.2.1.0~2,6~]dec-4-en-8-yl 2-methylpropanoate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR,10RS) isomer, 6-ethyl-2,10,10-trimethyl-1-oxaspiro[4.5]deca-3,6-diene, 1,2,3,5,6,7-hexahydro-1,1,2,3,3-pentamethyl-4-indenone (origin: International Flavors and Fragrances, USA), a mixture of 3-(3,3-dimethyl-5-indanyl)propanal and 3-(1,1-dimethyl-5-indanyl)propanal (origin: Firmenich SA, Geneva, Switzerland), 3',4-dimethyl-tricyclo[6.2.1.0(2,7)]undec-4-ene-9-spiro-2'-oxirane (origin: Firmenich SA, Geneva, Switzerland), 9/10-ethyldiene-3-oxatricyclo[6.2.1.0(2,7)]undecane, (perhydro-5,5,8A-trimethyl-2-naphthalenyl acetate (origin: Firmenich SA, Geneva, Switzerland), octalynol, (dodecahydro-3a,6,6,9a-tetramethyl-naphtho[2,1-b]furan, origin: Firmenich SA, Geneva, Switzerland), tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, pinene, camphene, 8-methoxycedrane, (8-methoxy-2,6,6,8-tetramethyl-tricyclo[5.3.1.0(1,5)]undecane (origin: Firmenich SA, Geneva, Switzerland), cedrene, cedrenol, cedrol, mixture of 9-ethylidene-3-oxatricyclo[6.2.1.0(2,7)]undecan-4-one and 10-ethylidene-3-oxatricyclo[6.2.1.0(2,7)]undecan-4-one (origin: Firmenich SA, Geneva, Switzerland), 3-methoxy-7,7-dimethyl-10-methylene-bicyclo[4.3.1]decane (origin: Firmenich SA, Geneva, Switzerland);

Group 6: (trimethyl-13-oxabicyclo-[10.1.0]-trideca-4,8-diene (origin: Firmenich SA, Geneva, Switzerland), Ambrettolide LG ((E)-9-hexadecen-16-olide, origin: Firmenich SA, Geneva, Switzerland), pentadecenolide (origin: Firmenich SA, Geneva, Switzerland), muscenone (3-methyl-(4/5)-cyclopentadecenone, origin: Firmenich SA, Geneva, Switzerland), 3-methylcyclopentadecanone (origin: Firmenich SA, Geneva, Switzerland), pentadecanolide (origin: Firmenich SA, Geneva, Switzerland), cyclopentadecanone (origin: Firmenich SA, Geneva, Switzerland), 1-ethoxyethoxy) cyclododecane (origin: Firmenich SA, Geneva, Switzerland), 1,4-dioxacycloheptadecane-5,17-dione, 4,8-cyclododecadien-1-one;

Group 7: (+−)-2-methyl-3-[4-(2-methyl-2-propanyl)phenyl]propanal (origin: Givaudan SA, Vernier, Switzerland), 2,2,2-trichloro-1-phenylethyl acetate.

Preferably, the perfume comprises at least 30%, preferably at least 50%, more preferably at least 60% of ingredients selected from Groups 1 to 7, as defined above. More preferably said perfume comprises at least 30%, preferably at least 50% of ingredients from Groups 3 to 7, as defined above. Most preferably said perfume comprises at least 30%, preferably at least 50% of ingredients from Groups 3, 4, 6 or 7, as defined above.

According to another preferred embodiment, the perfume comprises at least 30%, preferably at least 50%, more preferably at least 60% of ingredients having a log P above 3, preferably above 3.5 and even more preferably above 3.75.

Preferably, the perfume used in the invention contains less than 10% of its own weight of primary alcohols, less than 15% of its own weight of secondary alcohols and less than 20% of its own weight of tertiary alcohols. Advantageously, the perfume used in the invention does not contain any primary alcohols and contains less than 15% of secondary and tertiary alcohols.

According to an embodiment, the oil phase (or the oil-based core) comprises:
- 25-100 wt % of a perfume oil comprising at least 15 wt % of high impact perfume raw materials having a Log T<−4, and
- 0-75 wt % of a density balancing material having a density greater than 1.07 $g/cm^3$.

The nature of high impact perfume raw materials having a Log T<−4 and density balancing material having a density greater than 1.07 $g/cm^3$ are described in WO 2018/115250, the content of which is included by reference.

The term "biocide" refers to a chemical substance capable of killing living organisms (e.g. microorganisms) or reducing or preventing their growth and/or accumulation. Biocides are commonly used in medicine, agriculture, forestry, and in industry where they prevent the fouling of, for example, water, agricultural products including seed, and oil pipelines. A biocide can be a pesticide, including a fungicide, herbicide, insecticide, algicide, molluscicide, miticide and rodenticide; and/or an antimicrobial such as a germicide, antibiotic, antibacterial, antiviral, antifungal, antiprotozoal and/or antiparasite.

As used herein, a "pest control agent" indicates a substance that serves to repel or attract pests, to decrease, inhibit or promote their growth, development or their activity. Pests refer to any living organism, whether animal, plant or fungus, which is invasive or troublesome to plants or animals, pests include insects notably arthropods, mites, spiders, fungi, weeds, bacteria and other microorganisms.

According to a particular embodiment, the hydrophobic material is free of any active ingredient (such as perfume). According to this particular embodiment, it comprises, preferably consists of hydrophobic solvents, preferably chosen from the group consisting of isopropyl myristate, tryglycerides (e.g. Neobee® MCT oil, vegetable oils), D-limonene, silicone oil, mineral oil, and mixtures thereof with optionally hydrophilic solvents preferably chosen from the group consisting of 1,4-butanediol, benzyl alcohol, triethyl citrate, triacetin, benzyl acetate, ethyl acetate, propylene glycol (1,2-propanediol), 1,3-propanediol, dipropylene glycol, glycerol, glycol ethers and mixtures thereof.

According to any one of the invention's embodiments, the hydrophobic material represents between about 10% and 60% w/w, or even between 15% and 45% w/w, by weight, relative to the total weight of the dispersion as obtained after step c).

According to a particular embodiment, the oil phase essentially consists of the polyfunctional monomer, the cleavable multi-alcohol and a perfume or flavor oil.

Polyfunctional Monomer

According to an embodiment, the polyfunctional monomer is chosen from the group consisting of at least one polyisocyanate, poly maleic anhydride, poly acid chloride, polyepoxide, polyacrylate, polymethacrylate, polyalkoxysilane and mixture thereof.

The polyfunctional monomer used in the process according to the invention is present in amounts representing from 0.1 to 15%, preferably from 0.5 to 10% and more preferably from 0.8 to 6%, and even more preferably between 1 and 3% by weight based on the total amount of the oil phase.

According to a particular embodiment, the monomer added in step a) is at least one polyisocyanate having at least two isocyanate functional groups.

Suitable polyisocyanates used according to the invention include aromatic polyisocyanates, aliphatic polyisocyanates and mixtures thereof. Said polyisocyanates comprise at least 2, preferably at least 3 but may comprise up to 6, or even only 4, isocyanate functional groups. According to a particular embodiment, a triisocyanate (3 isocyanate functional groups) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

According to an embodiment, the at least one polyisocyanate used in the process of the invention is present in amounts representing from 0.1 to 15%, preferably from 0.5 to 10% and more preferably from 0.8 to 6%, and even more preferably between 1 and 3% by weight based on the total amount of the oil phase.

According to another embodiment, the polyfunctional polymer used in the present invention is a poly acid chloride.

According to an embodiment, the poly acyl chloride is chosen from the group consisting of benzene-1,3,5-tricarbonyl chloride, benzene-1,2,4-tricarbonyl trichloride, benzene-1,2,4,5-tetracarbonyl tetrachloride, cyclohexane-1,3,5-tricarbonyl trichloride, isophthalyol dichloride, diglycolyl dichloride, succinic dichloride, terephthaloyl chloride and mixtures thereof.

According to a particular embodiment, the poly acyl chloride is 1,3,5-benzene tricarbonyl chloride.

According to a particular embodiment, the poly acyl chloride has the following formula (II)

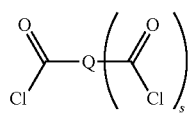

(II)

wherein s is an integer varying between 1 and 8, preferably between 1 and 6, more preferably between 1 and 4, and wherein Q is either an (s+1)-valent $C_3$ to $C_6$ alkyl group, or an (s+1)-valent $C_2$ to $C_{45}$ hydrocarbon group comprising at least one group selected from (i) to (vi),

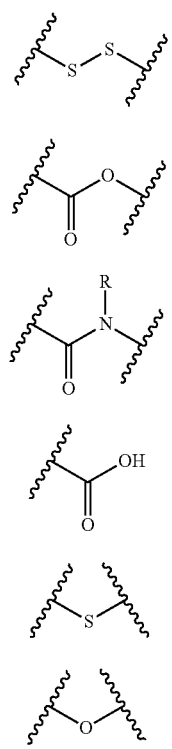

(i)

(ii)

(iii)

(iv)

(v)

(vi)

wherein R is a hydrogen atom or a methyl or ethyl group, preferably a hydrogen atom.

According to an embodiment, if the hydrocarbon group Q comprises several groups selected from (i) to (vi), they are each separated by at least one carbon atom of Q.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynil group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

It is understood that with the term " . . . a hydrocarbon group, possibly comprising . . . " it is meant that said hydrocarbon group optionally comprises heteroatoms to form ether, thioether, amine, nitrile or carboxylic acid groups. These groups can either substitute a hydrogen atom of the hydrocarbon group and thus be laterally attached to said hydrocarbon, or substitute a carbon atom (if chemically possible) of the hydrocarbon group and thus be inserted into the hydrocarbon chain or ring.

According to an embodiment, when group (vi) is present, it is only present in combination with either one of groups (i) to (v).

According to a particular embodiment, the acyl chloride is chosen from the group consisting of propane-1,2,3-tricarbonyl trichloride, cyclohexane-1,2,4,5-tetracarbonyl tetrachloride, 2,2'-disulfanediyldisuccinyl dichloride, 2-(2-chloro-2-oxo-ethyl)sulfanylbutanedioyl dichloride, (4-chloro-4-oxobutanoyl)-L-glutamoyl dichloride, (S)-4-((1,5-dichloro-1,5-dioxopentan-2-yl)amino)-4-oxobutanoic acid, 2,2-bis[(4-chloro-4-oxo-butanoyl)oxymethyl]butyl 4-chloro-4-oxo-butanoate, [2-[2,2-bis[(4-chloro-4-oxo-butanoyl)oxymethyl]butoxymethyl]-2-[(4-chloro-4-oxo-butanoyl)oxymethyl]butyl] 4-chloro-4-oxo-butanoate, 2,2-bis[(2-chlorocarbonylbenzoyl)oxymethyl]butyl 2-chlorocarbonyl-benzoate, [2-[2,2-bis[(2-chlorocarbonyl-benzoyl)oxymethyl]butoxymethyl]-2-[(2-chlorocarbonyl-benzoyl)oxymethyl]butyl] 2-chlorocarbonylbenzoate, 4-(2,4,5-trichlorocarbonylbenzoyl)oxybutyl 2,4,5-trichlorocarbonyl-benzoate, and mixtures thereof.

Step b): Preparing a Dispersing Phase, Wherein the Dispersing Phase is not Miscible with the Oil Phase There is no restriction regarding the nature of the solvent that can be used in step b) as long as it can dissolve the stabilizer.

According to a particular embodiment, the dispersing phase comprises, preferably consists of water.

According to another particular embodiment, the content of water is below or equal to 10%, preferably below or equal to 5%, more preferably below or equal to 3% by weight based on the total weight of the dispersing phase.

According to a particular embodiment, the dispersing phase is free of water.

According to an embodiment, the dispersing phase comprises a solvent chosen from the group consisting of glycerol, 1,4-butanediol, ethylene glycol and mixtures thereof.

Step c): Adding the Oil Phase into the Dispersing Phase to Form a Two-Phase Dispersion According to the invention, a stabilizer is added in the dispersing phase and/or the oil phase to stabilize the emulsion.

Said stabilizer can be an ionic or non-ionic emulsifier or a colloidal stabilizer.

The stabilizer can be a molecular emulsifier (standard emulsion) or solid particle emulsifier (Pickering emulsion).

"Stabilizer" and "emulsifier" are used indifferently in the present invention.

According to an embodiment, the stabilizer is chosen from the group consisting of gum Arabic, modified starch, polyvinyl alcohol (PVOH), polyvinylpyrolidone (PVP), carboxymethylcellulose (CMC), anionic polysaccharides, acrylamide copolymer, inorganic particles, protein such as soy protein, rice protein, whey protein, white egg albumin, sodium caseinate, gelatin, bovine serum albumin, hydrolyzed soy protein, hydrolyzed sericin, pseudocollagen, silk protein, sericin powder, and mixtures thereof.

When the stabilizer is added to the oil phase, it is preferably chosen from the group consisting of proteins such as soy protein, rice protein, whey protein, white egg albumin, sodium caseinate, gelatin, bovine serum albumin, hydrolyzed soy protein, hydrolyzed sericin, pseudocollagen, silk protein, sericin powder, and mixtures thereof.

When added to the oil phase, the stabilizer can be pre-dispersed in an inert solvent such as benzyl benzoate or can be mixed to the active ingredient, preferably comprising a perfume oil.

When the stabilizer is added to the water phase, it is preferably chosen from the group consisting of gum Arabic, modified starch, polyvinyl alcohol (PVOH), polyvinylpyrolidone (PVP), carboxymethylcellulose (CMC), anionic polysaccharides, acrylamide copolymer, inorganic particles, protein such as soy protein, rice protein, whey protein, white egg albumin, sodium caseinate, gelatin, bovine serum albumin, hydrolyzed soy protein, hydrolyzed sericin, pseudocollagen, silk protein, sericin powder, and mixtures thereof.

According to any one of the above embodiments of the present invention, the dispersion comprises between about 0.01% and 3.0% of a stabilizer, percentage being expressed on a w/w basis relative to the total weight of the oil-in-water emulsion as obtained after step c). In still another aspect of the invention, the dispersion comprises at least between about 0.05% and 1.0% of a colloid stabilizer. In still another aspect of the invention, the dispersion comprises between about 0.1% and 0.8% of a stabilizer.

Step d): Optionally, Adding a Reactant to the Dispersion Obtained in Step c)

Among the reactants that can be used in the invention, one may cite nucleophile compounds.

According to the invention, a nucleophile compound is defined as a chemical species that donates an electron pair to an electrophile to form a chemical bond in relation to a reaction.

The nucleophile compound may be chosen from the group consisting of nitrogen nucleophile, sulfur nucleophile, oxygen nucleophile, carbon nucleophile, phosphor nucleophile, and mixtures thereof.

Nitrogen nucleophile compounds may have at least one functional group chosen from the group consisting of ammonia, azides, amines, nitrites, hydroxylamines, hydrazins, carbazides, phenylhydrazines, semicarbazides, and amides, and mixtures thereof.

Sulfur nucleophile compounds may have at least one functional group chosen from the group consisting of hydrogen sulfide and its salts, thiols (RSH), thiolate anions (RS—), anions of thiolcarboxylic acids (RC(O)—S—), and anions of dithiocarbonates (RO—C(S)—S—) and dithiocarbamates (R$_2$N—C(S)—S—) and mixtures thereof.

Oxygen nucleophile compounds may have at least one functional group chosen from the group consisting of water, hydroxide anion, alcohols, alkoxide anions, carboxylate anions, carbonates, sulfonate, sulfates, sodium phosphates, sodium silicates, borax, sodium tetraborate, and mixtures thereof.

Carbon nucleophile compounds may have at least one functional group chosen from the group consisting of enols, enols carbon nucleophiles, malonates and acetoacetates.

Phosphor nucleophile compounds may have at least one functional group chosen from the group consisting of phosphines, phosphite anions and mixture thereof.

According to a particular embodiment, the reactant is chosen from the group consisting of xylylene diamine, 1,2-diaminocyclohexane, 1,4-diaminocyclohexane, L-lysine, L-lysine ethyl ester, O,O'-bis(2-aminopropyl)polypropylene glycol-block-polyethylene glycol-block-polypropylene glycol, ethylene diamine, 1,3-diamino-2-hydroxypropane, diethylene triamine, spermine, spermidine, cystamine, cystine, cystine dialkyl ester, aminoguanidine bicarbonate, N,N'-diethylethylenediamine, polyamidoamine (PAMAM), chitosan, 3-aminopropyltriethoxysilane, L-arginine, 1,3-diaminopropane, N-ethylguanidine sulfate, 1,6-diaminohexane, guanidine salts, N,N,N',N'-tetrakis(3-aminopropyl)-1,4-butanediamine, guanazole, 2-amino-1,3-propanediol, ethanolamine tris(2-aminoethyl)amine, tris(3-aminopropyl)amine, tris[2-(methylamino)ethyl]amine, 1-(2-aminoethyl)piperazine, triethylenetetramine, triethanolamine, phthalic acid dipotassium salt, succinic acid disodium salt, dithiothreitol and mixtures thereof.

According to the invention, at least one cleavable multi-alcohol of formula (I) is added in step a) and/or in step b) and/or in step c) and/or in step d). When added in step a), the multi-alcohol can be added to the oil phase in addition to the polyfunctional monomer as a separate component or in the form of a reaction product between at least one cleavable multi-alcohol and the polyfunctional monomer.

According to an embodiment, step a) consists of adding the reaction product between said cleavable multi-alcohol and at least one polyfunctional monomer in a hydrophobic material. According to another embodiment, step a) consists of adding at least one cleavable multi-alcohol and at least one polyfunctional monomer in a hydrophobic material.

Cleavable Multi-Alcohol

According to the invention, the cleavable multi-alcohol has the following formula (I)

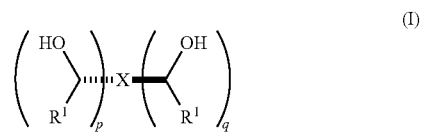

wherein each $R^1$ is independently H or $CH_2OH$ and wherein p and q are integers varying between 1 and 3, preferably p and q are either 1 or 2, and wherein X is a C₂ to C₃₀ hydrocarbon group, possibly comprising one to ten heteroatoms, selected from O, S and N to form ether, ester, carboxylic acid, aldehyde, ketone, alcohol, thiol, disulfide, thioether, thioester, carbamate, amide, oxime, imine, amine or nitrile functional groups.

According to the invention, X can be split into at least two separate pieces by the cleavage of one or several covalent bonds as the consequence of a redox-reaction, hydrolysis, a retro-1,4-addition, the action of light and/or combinations thereof.

According to an embodiment, X is a compound chosen from the group consisting of disulfides, oxazolidines, imines, 1,4-addition products, carbonates and aryl ketone derivatives.

Preferably, X is selected from the group consisting of (a)
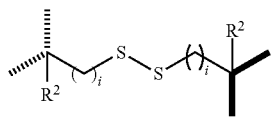

(b)
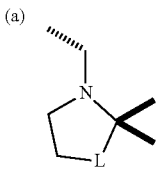

(c)
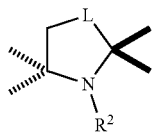

(d)
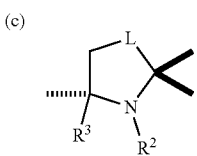

(e)
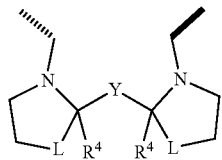

(f)
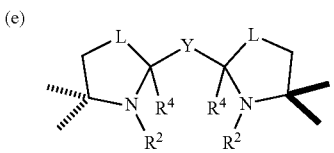

(g)
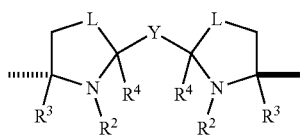

(h)
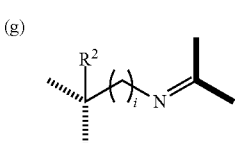

(i)
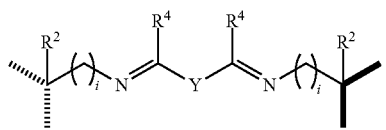

(j)
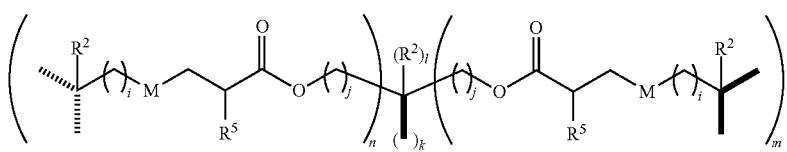

(k)
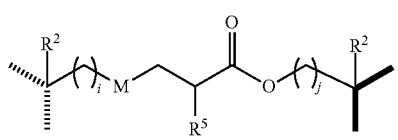

(l)
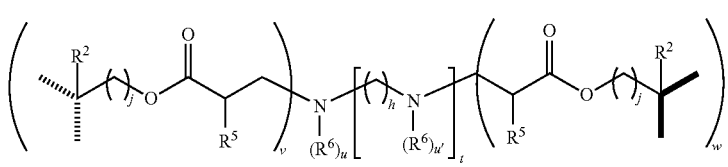

-continued (m)
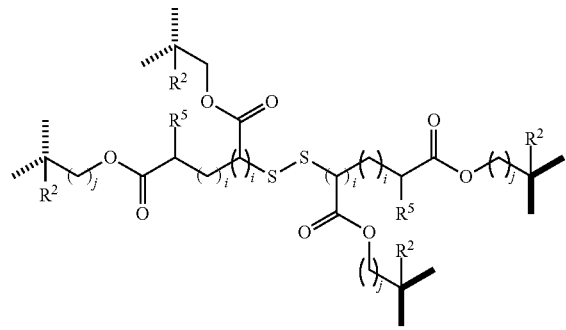

(n)
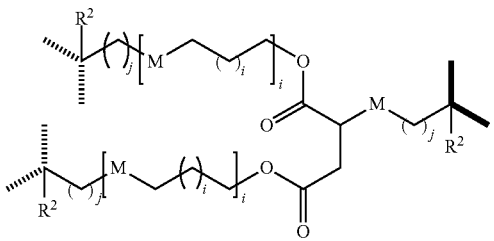

(o)
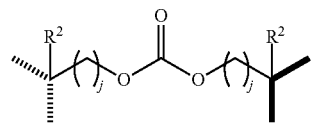

(p)
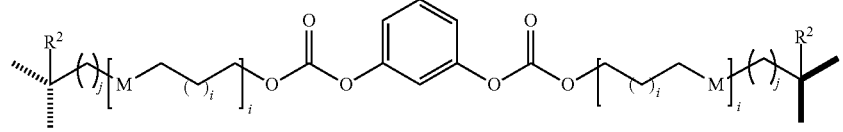

(q)
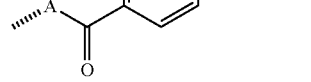

(r)
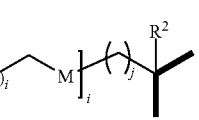

with L being a O or a S atom or a NH group, preferably a O atom, M being a S atom or a $NR^6$ group, preferably a S atom, Y being a $CH_2$, a $CH_2$—$CH_2$ or a phenyl group, Z being a $O(CH_2)_xO$ or a $(CH_2)_x$ group with x being an integer varying between 1 and 4, and A being a $COOCH_2(CR^2R^2)_i$, $CHR^2OCH_2(CR^2R^2)_i$ or $(CR^2R^2)(CHR^2)_x$ group, with each $R^2$ being independently a H, $CH_3$, $CH_2CH_3$, $CH_2OH$ or $CH_2CH_2OH$ group and each $R^3$ being independently a $CH_3$ or $CH_2CH_3$ group, with $R^4$ being either H or $CH_3$ or, if Y is not phenyl group, then two $R^4$ taken together may represent a $CH_2$ or a $CH_2$—$CH_2$ group, with $R^5$ being either H or $CH_3$, with $R^6$ being either H, a $C_1$-$C_6$ alkyl group or a $CH_2$—$CH_2$—$(CH_2)_j$—OH group, if t=1 two $R^6$ taken together might form a $CH_2$—$CH_2$—$(CH_2)_j$ group, with h being an integer varying between 1 and 6, each i being individually of each other 0 or 1, each j being individually of each other an integer varying between 0 and 2, and with k and l being integers varying between 0 and 2, and m and n being 1 or 2, with the proviso that k+l+m+n=4, with t, u and u' being 0 or 1, v and w being 1 or 2, and with the proviso that u+v+w=3 (if t=0) or u+u'+v+w=4 (if t=1), and wherein the hatched and the bold lines are either linked to a hydrogen atom or indicate the bond between said X and the $(CHR^1OH)_p$ (hatched line) or $(CHR^1OH)_q$ (bold line) groups of the multi-alcohol of formula (I), with the proviso that at least one hatched and at least one bold line of X are linked to a $CHR^1OH$ group.

According to an embodiment, the cleavable multi-alcohol is a compound chosen from the group consisting of disulfides, oxazolidines, imines/Schiff bases, 1,4-Addition products, carbonates, aryl ketone derivatives and mixtures thereof.

Non-limiting examples of multi-alcohols are compounds chosen from the group consisting of:

disulfides chosen from the group consisting of 2,2'-disulfanediylbis(ethan-1-ol), 2,2'-disulfanediylbis(propane-1,3-diol), 3-(2,3-dihydroxypropyldisulfanyl)propane-1,2-diol, 2,2'-(disulfanediylbis(methylene))bis(2-methylpropane-1,3-diol) or 2,2'-(disulfanediylbis(methylene))bis(2-ethylpropane-1,3-diol), bis(3-hydroxy-2-(hydroxymethyl)-2-methylpropyl) 3,3'-disulfanediyldipropionate, tetrakis(2-hydroxyethyl)2,2'-disulfanediyldisuccinate, and/or oxazolidines chosen from the group consisting of (3-(2-hydroxyethyl)oxazolidine-2,2-diyl)dimethanol, oxazolidine-2,2,4-triyltrimethanol, 2,2'-(ethane-1,2-diylbis(2-methyloxazolidine-2,3-diyl))bis(ethan-1-ol), (ethane-1,2-diylbis(2-methyloxazolidine-2,4,4-triyl))
tetramethanol, 2,2'-(1,4-phenylenebis(oxazolidine-2,3-diyl))bis(ethan-1-ol), 2,2'-(furan-2,5-diylbis(oxazolidine-2,3-diyl))bis(ethan-1-ol), 2,2'-(cyclohexane-1,4-diylbis(oxazolidine-2,3-diyl))bis(ethan-1-ol), 2,2'-(1,9-dioxa-4,12-diazadispiro[4.2.4$^8$.2$^5$]tetradecane-4,12-diyl)bis(ethan-1-ol), (1,4-phenylenebis(oxazolidine-2,4,4-triyl))tetramethanol, (1,9-dioxa-4,12-diazadispiro[4.2.4$^8$.2$^5$]tetradecane-3,3,11,11-tetrayl)tetramethanol, (1,9-dioxa-4,12-diazadispiro[4.2.4$^8$.2$^5$]tetradecane-3,11-diyl)dimethanol, (3,11-diethyl-1,9-dioxa-4,12-diazadispiro[4.2.4$^8$.2$^5$]tetradecane-3,11-diyl)dimethanol, (1,4-phenylenebis(4-ethyloxazolidine-2,4-diyl))dimethanol, (3,11-diethyl-1,9-dioxa-4,12-diazadispiro[4.2.4$^8$.2$^5$]tetradecane-3,11-diyl)dimethanol, 2,2'-(3,11-bis(hydroxymethyl)-1,9-dioxa-4,12-diazadispiro[4.2.4$^8$.2$^5$]tetradecane-4,12-diyl)bis(ethan-1-ol) and/or imines and Schiff bases chosen from the group consisting of 2,2'-((1,4-phenylenebis(methanylylidene))bis(azanylylidene))bis(propane-1,3-diol), 2,2'-((furan-2,5-diylbis(methanylylidene))bis(azanylylidene))bis(propane-1,3-diol), and/or 1,4-Addition products chosen from the group consisting of 2-hydroxyethyl 3-((2-hydroxyethyl)thio)propanoate, 3-hydroxy-2-(hydroxymethyl)-2-methylpropyl 3-((3-hydroxy-2-(hydroxymethyl)-2-methylpropyl)thio)-2-methylpropanoate, 3-hydroxy-2-(hydroxymethyl)-2-methylpropyl (S)-3-((2,3-dihydroxypropyl)thio) propanoate, 2-ethyl-2-(((3-((2-hydroxyethyl)thio) propanoyl)oxy)methyl)propane-1,3-diyl bis(3-((2-hydroxyethyl)thio)propanoate), 4-hydroxybutyl 3-((1,3-dihydroxypropan-2-yl)amino)propanoate, bis(2-hydroxyethyl) 3,3'-(butylazanediyl)dipropionate, bis(2-hydroxyethyl) 3,3'-((4-hydroxybutyl)azanediyl) dipropionate, bis(2-hydroxyethyl) 3,3'-(piperazine-1,4-diyl)dipropionate, tetrakis(2-hydroxyethyl) 3,3',3'',3'''-(propane-1,3-diylbis(azanetriyl))tetrapropionate, bis(3-((2-hydroxyethyl)thio)propyl) 2-((2-hydroxyethyl)thio)succinate, and/or carbonates chosen from the group consisting of bis(2,3-dihydroxypropyl)carbonate, bis(3-hydroxy-2-(hydroxymethyl)-2-methylpropyl)carbonate, benzene-1,3,5-triyl tris(3-((2-hydroxyethyl)thio)propyl) tricarbonate, and/or aryl ketone derivatives chosen from the group consisting of bis(2-hydroxyethyl) 2,2'-(methylenebis(4,1-phenylene))bis(2-oxoacetate), bis(2,2-bis(hydroxymethyl) butyl) 2,2'-(methylenebis(4,1-phenylene))bis(2-oxoacetate), bis(2-hydroxyethyl) 2,2'-(ethane-1,2-diylbis(4,1-phenylene))bis(2-oxoacetate), bis(3-hydroxy-2-(hydroxymethyl)-2-methylpropyl) 2,2'-(1,4-phenylene) bis(2-oxoacetate), 1,1'-(1,4-phenylene)bis(5-hydroxypentan-1-one), and mixtures thereof.

According to a particular embodiment, the cleavable multi-alcohol is not trimethylol propane.

According to an embodiment, the monomer is present in the hydrophobic material at a concentration comprised between 0.01% and 50%, preferably between 0.02% and 20%, more preferably between 0.1% and 10% and even more preferably between 0.5% and 5%. A cleavable multi-alcohol compound of the invention is added to the slurry to obtain a molar ratio between the OH group of the said cleavable multi-alcohol compound and the functional group of the said monomer between 0.01 and 10, more preferably between 0.1 and 5, more preferably between 0.2 and 1 and even more preferably between 0.25 and 0.75.

The choice of the structure of a multi-alcohol according to formula (I) for the preparation of a given polymer will depend on the conditions of the polymerization reaction. This means, that not any multi-alcohol is necessarily the most suitable monomer for all kinds of polymerization reactions. As an example, if a polymerization reaction is carried out under strongly hydrolyzing conditions, i.e. at very high or very low pH, then readily hydrolysable multi-alcohols might be less favorable than others that are less easily cleaved under the reaction conditions. In such a case, multi-alcohols that are cleaved under the influence of light, or redox-reactions might be preferable. Similarly, if light-induced polymerization reactions are used, hydrolytically cleavable multi-alcohols might be preferable over light-sensitive structures.

Step e): Performing a Curing Step to Form Core-Shell Microcapsules in the Form of a Slurry The curing step e) allows ending up with microcapsules in the form of a slurry.

According to a preferred embodiment, to enhance the kinetics, said step is performed at a temperature comprised between 60 and 80° C., possibly under pressure, for 1 to 4 hours. More preferably it is performed at between 50 and 90° C. for between 30 minutes and 4 hours. However, the curing step can take place at room temperature.

Optional Step: Optional Outer Coating

According to a particular embodiment of the invention, at the end of step e) or during step e), one may also add to the invention's slurry a polymer selected from the group consisting of a non-ionic polysaccharide, a cationic polymer and mixtures thereof to form an outer coating to the microcapsule.

Non-ionic polysaccharide polymers are well known to a person skilled in the art and are described for instance in WO2012/007438 page 29, lines 1 to 25 and in WO2013/026657 page 2, lines 12 to 19 and page 4, lines 3 to 12. Preferred non-ionic polysaccharides are selected from the group consisting of locust bean gum, xyloglucan, guar gum, hydroxypropyl guar, hydroxypropyl cellulose and hydroxypropyl methyl cellulose.

Cationic polymers are well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 1.5M Dalton. According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also Jaguar® (C13S or C17, origin Rhodia).

According to any one of the above embodiments of the invention, there is added an amount of polymer described above comprised between about 0% and 5% w/w, or even between about 0.1% and 2% w/w, percentage being expressed on a w/w basis relative to the total weight of the slurry as obtained after step d). It is clearly understood by a person skilled in the art that only part of said added polymers will be incorporated into/deposited on the microcapsule shell.

Process for Preparing Microcapsule Powder

Another object of the invention is a process for preparing a microcapsule powder comprising the steps as defined above and an additional step consisting of submitting the slurry obtained in step e) or f) to a drying process, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, vegetable gums, pectins, xanthans, alginates, carragenans or cellulose derivatives to provide microcapsules in a powder form.

However, one may cite also other drying method such as the extrusion, plating, spray granulation, the fluidized bed, or even a drying at room temperature using materials (carrier, desiccant) that meet specific criteria as disclosed in WO2017/134179.

According to a particular embodiment, the carrier material contains free perfume oil which can be the same or different from the perfume from the core of the microcapsules.

According to a particular embodiment, the carrier material contains free perfume oil which can be the same or different from the perfume from the core of the microcapsules.

Another object of the invention is a solid particle comprising:
  a carrier material, preferably a polymeric carrier material chosen from the group consisting of polyvinyl acetate, polyvinyl alcohol, dextrins, natural or modified starch, vegetable gums, pectins, xanthans, alginates, carragenans, cellulose derivatives and mixtures thereof, and
  microcapsules as defined above entrapped in said carrier material, and
  optionally free perfume entrapped in said carrier material.

Solid particle as defined above and microcapsule powder can be used indifferently in the present invention.

Multiple Capsule System

According to an embodiment, the microcapsules of the invention (first type of microcapsule) can be used in combination with a second type of microcapsules.

Another object of the invention is a microcapsule delivery system comprising:
  the microcapsules of the present invention as a first type of microcapsules, and
  a second type of microcapsules, wherein the first type of microcapsule and the second type of microcapsules differ in their hydrophobic material and/or their wall material and/or in their coating material.

Microcapsule Slurry

Another object of the invention is a microcapsule slurry obtainable by the process as described above.

The composition of the shell enables to provide microcapsules that show the desired stability in the product base (e.g. counteracts efficiently the extraction of the perfume by the surfactants of the consumer product).

Thus, another object of the invention is a core-shell microcapsule or a core-shell microcapsule slurry having at least one core-shell microcapsule, said core-shell microcapsule comprising:
  an oil-based core comprising a hydrophobic material, preferably a perfume, and
  a shell comprising a reaction product between a polyfunctional monomer and a cleavable multi-alcohol,
  wherein the cleavable multi-alcohol has the following formula (I)

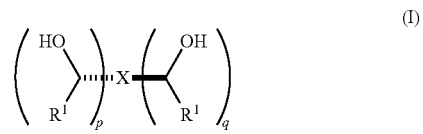

wherein each $R^1$ is independently H or $CH_2OH$ and wherein p and q are integers varying between 1 and 3, preferably p and q are either 1 or 2, and wherein X is a $C_2$ to $C_{30}$ hydrocarbon group, possibly comprising one to ten heteroatoms, selected from O, S and N to form ether, ester, carboxylic acid, aldehyde, ketone, alcohol, thiol, disulfide, thioether, thioester, carbamate, amide, oxime, imine, amine or nitrile functional groups.

The embodiments and definitions described previously (e.g, hydrophobic material, polyfunctional monomer, cleavable multi-alcohol) for the process also apply for the microcapsules.

Copolymer

A copolymer comprising a reaction product between a polyfunctional monomer and at least one cleavable multi-alcohol as defined above is also an object of the present invention.

The embodiments described previously regarding also apply for the microcapsules and the copolymer disclosed previously.

Perfuming Composition and Consumer Products

The microcapsules of the invention can be used in combination with active ingredients. An object of the invention is therefore a composition comprising:
  (i) microcapsules as defined above;
  (ii) an active ingredient, preferably chosen in the group consisting of a cosmetic ingredient, skin caring ingredient, perfume ingredient, flavor ingredient, malodour counteracting ingredient, bactericide ingredient, fungicide ingredient, pharmaceutical or agrochemical ingredient, a sanitizing ingredient, an insect repellent or attractant, and mixtures thereof.

The capsules of the invention show a good performance in terms of stability in challenging medium.

Another object of the present invention is a perfuming composition comprising:
(i) microcapsules or microcapsule slurry as defined above, wherein the oil comprises a perfume;
(ii) at least one ingredient selected from the group consisting of a perfumery carrier, a perfumery co-ingredient and mixtures thereof,
(iii) optionally at least one perfumery adjuvant.

As liquid perfumery carriers one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words, such a co-ingredient, to be considered as being a perfuming one, must be recognized by a person skilled in the art as being able to at least impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.01 and 30% by weight of microcapsules as defined above.

The invention's microcapsules can advantageously be used in many application fields and used in consumer products. Microcapsules can be used in liquid form applicable to liquid consumer products as well as in powder form, applicable to powder consumer products.

According to a particular embodiment, the consumer product as defined above is liquid and comprises:
a) from 2 to 65% by weight, relative to the total weight of the consumer product, of at least one surfactant;
b) water or a water-miscible hydrophilic organic solvent; and
c) microcapsules or a microcapsule slurry as defined above,
d) optionally non-encapsulated perfume.

According to a particular embodiment, the consumer product as defined above is in a powder form and comprises:
a) from 2 to 65% by weight, relative to the total weight of the consumer product, of at least one surfactant;
b) a microcapsule powder as defined above.
c) optionally perfume powder that is different from the microcapsules defined above.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care, surface care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsules than those here-disclosed.

In particular a liquid consumer product comprising:
a) from 2 to 65% by weight, relative to the total weight of the consumer product, of at least one surfactant;
b) water or a water-miscible hydrophilic organic solvent; and
c) a perfuming composition as defined above is another object of the invention.

Also, a powder consumer product comprising
(a) from 2 to 65% by weight, relative to the total weight of the consumer product, of at least one surfactant; and
(b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc.). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumed consumer products can be a perfume, such as a fine perfume, a cologne, an after-shave lotion, a body-splash; a fabric care product, such as a liquid or solid detergent, tablets and pods, a fabric softener, a dryer sheet, a fabric refresher, an ironing water, or a bleach; a personal-care product, such as a hair-care product (e.g. a shampoo, hair conditioner, a coloring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.); a hygiene product such as sanitary napkins, diapers, toilet paper.

Another object of the invention is a consumer product comprising:
  a personal care active base, and
  microcapsules or microcapsule slurry as defined above or the perfuming composition as defined above,
wherein the consumer product is in the form of a personal care composition.

Personal care active bases in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

The personal care composition is preferably chosen from the group consisting of a hair-care product (e.g. a shampoo, hair conditioner, a coloring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product);

Another object of the invention is a consumer product comprising:
  a home care or a fabric care active base, and
  microcapsules or microcapsule slurry as defined above or the perfuming composition as defined above,
wherein the consumer product is in the form of a home care or a fabric care composition.

Home care or fabric care active bases in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Preferably, the consumer product comprises from 0.1 to 15 wt %, more preferably between 0.2 and 5 wt % of the microcapsules of the present invention, these percentages being defined by weight relative to the total weight of the consumer product. Of course the above concentrations may be adapted according to the benefit effect desired in each product.

Fabric Softener

An object of the invention is a consumer product in the form of a fabric softener composition comprising:
  a fabric softener active base; preferably chosen from the group consisting of dialkyl quaternary ammonium salts, dialkyl ester quaternary ammonium salts (esterquats), Hamburg esterquat (HEQ), TEAQ (triethanolamine quat), silicones and mixtures thereof, preferably in an amount comprised between 85 and 99.95% by weight based on the total weight of the composition,
  microcapsules or a microcapsule slurry as defined above, preferably in an amount comprised between 0.05 to 15 wt %, more preferably between 0.1 and 5 wt % by weight based on the total weight of the composition.

Liquid Detergent

An object of the invention is a consumer product in the form of a liquid detergent composition comprising:
  a liquid detergent active base; preferably chosen from the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, preferably in an amount comprised between 85 and 99.95% by weight based on the total weight of the composition,
  microcapsules or a microcapsule slurry as defined above, preferably in an amount comprised between 0.05 to 15 wt %, more preferably between 0.1 and 5 wt % by weight based on the total weight of the composition.

Solid Detergent

An object of the invention is a consumer product in the form of a solid detergent composition comprising:
  a solid detergent active base; preferably chosen from the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, preferably in an amount comprised between 85 and 99.95% by weight based on the total weight of the composition,
  microcapsules or a microcapsule slurry as defined above, preferably in an amount comprised between 0.05 to 15 wt %, more preferably between 0.1 and 5 wt % by weight based on the total weight of the composition.

Shampoo/Shower Gel

An object of the invention is a consumer product in the form of a shampoo or a shower gel composition comprising:
  a shampoo or a shower gel active base; preferably chosen from the group consisting of sodium alkylether sulfate, ammonium alkylether sulfates, alkylamphoacetate, cocamidopropyl betaine, cocamide MEA, alkylglucosides and aminoacid based surfactants and mixtures thereof, preferably in an amount comprised between 85 and 99.95% by weight based on the total weight of the composition, microcapsules or a microcapsule slurry as defined above, preferably in an amount comprised between 0.05 to 15 wt %, more preferably between 0.1 and 5 wt % by weight based on the total weight of the composition.

Rinse-Off Conditioner

An object of the invention is a consumer product in the form of a rinse-off conditioner composition comprising:
- a rinse-off conditioner active base; preferably chosen from the group consisting of cetyltrimonium chloride, stearyl trimonium chloride, benzalkonium chloride, behentrimonium chloride and mixture thereof, preferably in an amount comprised between 85 and 99.95% by weight based on the total weight of the composition,
- microcapsules or a microcapsule slurry as defined above, preferably in an amount comprised between 0.05 to 15 wt %, more preferably between 0.1 and 5 wt % by weight based on the total weight of the composition.

Hair Coloration

An object of the invention is a consumer product in the form of an oxidative hair coloring composition comprising:
- an oxidizing phase comprising an oxidizing agent and an alkaline phase comprising an alkaline agent, a dye precursor and a coupling compound; wherein said dye precursor and said coupling compound form an oxidative hair dye in the presence of the oxidizing agent, preferably in an amount comprised between 85 and 99.95% by weight based on the total weight of the composition,
- microcapsules or a microcapsule slurry as defined above, preferably in an amount comprised between 0.05 to 15 wt %, more preferably between 0.1 and 5 wt % by weight based on the total weight of the composition.

By "oxidative hair coloring composition", it is meant a composition comprising two groups of colorless dye molecules: the dye precursor and the coupling agent. Upon reaction with each other through an oxidation process, they form a wide range of colored molecules (dyes) that are then trapped into the hair due their size. In other words, the dye precursor and the coupling compound form an oxidative hair dye in the presence of the oxidizing agent.

"Dye precursor" and "oxidative dye precursor" are used indifferently in the present invention.

Dye precursors can be aromatic compounds derived from benzene substituted by at least two electron donor groups such as $NH_2$ and OH in para or ortho positions to confer the property of easy oxidation.

According to an embodiment, dye precursors are chosen from the group consisting of p-phenylene diamine, 2,5-diamino toluene, N,N-bis(2-hydroxymethyl)-p-phenylene diamine, 4-aminophenol, 1,4-diamino-benzene, and mixtures thereof.

The primary dye precursors is used in combination with coupling agents. Coupling agents are preferably aromatic compounds derived from benzene and substituted by groups such as $NH_2$ and OH in the meta position and do not produce color singly, but which modify the color, shade or intensity of the colors developed by the dye precursor.

According to an embodiment, the coupling agent is chosen from the group consisting of resorcinol, 2-methyl resorcinol, 4-chlororesorchinol, 2,5-diamino-toluene, 1,3-diamino-benzene, 2,4-diaminophenoxyethanol HCl, 2-aminohydroxyethylaminoanisole sulfate, 4-amino-2-hydroxytoluene, and mixtures thereof.

The oxidative dye precursor is preferably used in an amount comprised between 0.001% and 5%, preferably between 0.1% and 4% by weight based on the total weight of the composition.

The use of oxidative dye precursors and coupling agents in hair coloring formulation have been widely disclosed in the prior art and is well-known from the person skilled in the art. One may cite for example EP0946133A1, the content of which is incorporated by reference.

The alkaline phase comprises an alkaline agent, preferably chosen from the group consisting of ammonia hydroxide, ammonia carbonate, ethanolamine, potassium hydroxide, sodium borate, sodium carbonate, triethanolamine and mixtures thereof.

The alkaline agent is preferably used in an amount comprised between 1% and 10%, preferably between 3% and 9% by weight based on the total weight of the composition.

According to the invention, the coupling agent and the dye precursor in an alkaline medium form an oxidative hair dye in the presence of the oxidizing agent.

The oxidizing agent will supply the necessary oxygen gas to develop color molecules and create a change in hair color.

The oxidizing agent should be safe and effective for use in the compositions herein.

Preferably, the oxidizing agents suitable for use herein will be soluble in the compositions according to the present invention when in liquid form and/or in the form intended to be used.

Preferably, oxidizing agents suitable for use herein will be water-soluble. Suitable oxidizing agents for use herein are selected from inorganic peroxygen oxidizing agents, preformed organic peroxyacid oxidizing agents and organic peroxide oxidizing agents or mixtures thereof.

The oxidizing agent is preferably used in an amount comprised between 5 and 30%, preferably between 5 and 25% by weight based on the total weight of the composition.

Components commonly used in cosmetic compositions may be added into the hair coloring composition as defined in the present invention. One may cite for example, surfactants, cationic polymers, oily substances, silicone derivatives, free perfume, preservatives, ultraviolet absorbents, antioxidants, germicides, propellants, thickeners.

According to a particular embodiment, the hair coloring composition comprises one or more quaternary ammonium compounds, preferably chosen from the group consisting of cetyltrimonium chloride, stearyl trimonium chloride, benzalkonium chloride, behentrimonium chloride and mixture thereof to confer hair conditioner benefits.

Perfuming Composition

According to a particular embodiment, the consumer product is in the form of a perfuming composition comprising:
- 0.1 to 30%, preferably 0.1 to 20% of microcapsules or microcapsule slurry as defined previously,
- 0 to 40%, preferably 3-40% of perfume, and
- 20-90, preferably 40-90% of ethanol, by weight based on the total weight of the perfuming composition.

The invention will now be further described by way of examples. It will be appreciated that the invention as claimed is not intended to be limited in any way by these examples.

EXAMPLES

The invention is hereafter described in a more detailed manner by way of the following examples, wherein the abbreviations have the usual meaning in the art, temperatures are indicated in degrees centigrade (° C.). NMR spectral data were recorded on a Bruker AMX 500 spectrometer in deuterated dimethyl sulfoxide (DMSO)-$d_6$ at 500

MHz for $^1$H and at 125.8 MHz for $^{13}$C if not indicated otherwise, the chemical displacements δ are indicated in ppm with respect to $Si(CH_3)_4$ as the standard, the coupling constants J are expressed in Hz (br.=broad peak). Reactions were carried out in standard glassware under $N_2$. Commercially available reagents and solvents were used without further purification if not stated otherwise.

Although specific conformations or configurations are indicated for some of the compounds, this is not meant to limit the use of these compounds to the isomers described. According to the invention, all possible conformation or configuration isomers are expected to have a similar effect.

2,2'-Disulfanediylbis(ethan-1-ol) (Multi-Alcohol 1) is commercially available, other non-limiting examples of multi-alcohols according to formula (I) were prepared as described in Example 1.

Example 1

Preparation of Cleavable Multi-Alcohols According to Formula (I)

(a) Synthesis of 2,2'-disulfanediylbis(propane-1,3-diol) (Multi-Alcohol 2)

Amberlyst 15H (3.0 g) was added to a biphasic mixture of 1,3-di(tert-butyldimethylsilyloxy)-propane-2-thiol (38.1 g, 0.11 mol, prepared as described in J. E. Casida et al., Bioorganic & Medicinal Chemistry, 2010, 18, 1942-1947) and methanol (300 mL). After stirring at room temperature overnight, the suspension was filtered, rinsed with methanol (50 mL) and the filtrate concentrated to give 25.0 g of a biphasic mixture.

Adding acetone (50 mL) and heating to ca. 50° C. afforded a solution, which was left cooling to room temperature and placed in a freezer to crystallize. The solid was filtered off, washed with ice-cold acetone dried under vacuum (0.43 mbar) to give 3.4 g of white crystals. The mother liquor was concentrated, suspended in acetone (50 mL) and placed on an ice bath for 2 h. Filtration, rinsing with ice-cold acetone (25 mL) and drying under vacuum afforded another 4.0 g of white crystals as the target compound (30%).

$^1$H-NMR (CD$_3$OD): 4.83 (br. s, 4H), 3.78 (dd, J=5.9, 2.3, 8H), 2.93 (quint., J=6.1, 2H).

$^{13}$C-NMR (CD$_3$OD): 62.39, 57.89.

(b) Synthesis of (±)-3-(2,3-dihydroxypropyldisulfanyl)propane-1,2-diol (Multi-Alcohol 3)

Ferrous sulfate hydrate (FeSO$_4$×7 H$_2$O, 85 mg, 0.3 mmol) was added to a stirred solution of 3-mercaptopropane-1,2-diol (35 mL, 390.0 mmol) in water (35 mL). Then hydrogen peroxide (35%, 29.15 g, 300.0 mmol) was added dropwise during 20 min. The reaction was exothermic and the temperature was kept with an ice bath at ca. 40° C. during the addition of H$_2$O$_2$. After removing the ice bath, the reaction was left stirring for 5 h and then poured into a separation funnel containing ethyl acetate (100 mL). After extraction, the phases were separated and the aqueous layer re-extracted with ethyl acetate (100 mL) and the organic layer washed with water (50 mL). The aqueous phase was concentrated, then toluene (250 mL) was added and the mixture further concentrated. Drying under vacuum (0.14 mbar) afforded 44.0 g (quant.) of the crude product.

$^1$H-NMR: 4.53 (br. s, 4H), 3.69-3.62 (m, 2H), 3.46-3.29 (m, 4H), 2.95-2.87 (m, 2H), 2.75-2.66 (m, 2H).

$^{13}$C-NMR: 70.13, 70.10, 64.43, 64.42, 43.10, 43.05.

(c) Synthesis of 2,2'-(disulfanediylbis(methylene)) bis(2-methylpropane-1,3-diol) (Multi-Alcohol 4)

Ferrous sulfate hydrate (FeSO$_4$×7 H$_2$O, 28 mg, 0.04 mmol) was added at room temperature to a stirred emulsion of (2,2,5-trimethyl-1,3-dioxan-5-yl)methanethiol (8.81 g, 50.0 mmol) in water (50 mL). Then hydrogen peroxide (35%, 3.7 g, 38.5 mmol) was added dropwise (exothermic reaction). The mixture was left stirring overnight and then poured into a separation funnel containing ethyl acetate (100 mL). After extraction, the phases were separated and the aqueous layer re-extracted with ethyl acetate (100 mL) and the organic layer washed with water (50 mL) and a saturated aqueous solution of NaCl (50 mL), dried (Na$_2$SO$_4$) and concentrated to give 2.06 g (30%) of the target compound.

$^1$H-NMR (CD$_3$OD): 4.85 (s, 4H), 3.45 (s, 8H), 2.92 (s, 4H), 0.93 (s, 6H).

$^{13}$C-NMR (CD$_3$OD): 67.10, 46.84, 42.75, 18.86.

(d) Synthesis of (3-(2-hydroxyethyl)oxazolidine-2,2-diyl)dimethanol (Multi-Alcohol 5)

1,3-Dihydroxypropan-2-one (4.06 g, 50.0 mmol) was suspended in tetrahydrofuran (THF, 150 mL). Then 2,2'-azanediylbis(ethan-1-ol) (6.31 g, 60.0 mmol) and anhydrous Na$_2$SO$_4$ (10.0 g) were added. After stirring at room temperature for about 90 h, the reaction mixture was filtered and concentrated. The product was consecutively treated with cyclohexane (25 mL) which, after stirring for 15 min at 50° C., was decanted and toluene (50 mL) which, after stirring for 15 min at 50° C., was decanted. Concentrating the remaining product and drying under vacuum afforded 8.64 g of the crude product.

$^1$H-NMR (600 MHz): 4.48 (br. s, 1H), 4.33 (br. s, 2H), 3.80 (t, J=6.2, 2H), 3.45 (q, J=5.7, 2H), 3.34 (s, 4H), 2.99 (t, J=6.2, 2H), 2.79 (t, J=6.2, 2H).

$^{13}$C-NMR (151.0 MHz): 96.02, 64.44, 62.31, 60.28, 50.96, 50.79.

(e) Synthesis of (±)-oxazolidine-2,2,4-triyltrimethanol (Multi-Alcohol 6)

2-Aminopropane-1,3-diol (2.78 g, 30.0 mmol) was suspended in THF (75 mL). Then Na$_2$SO$_4$ (2.00 g, 14.1 mmol, previously dried in an oven at 150° C.) and 1,3-dihydroxypropan-2-one (2.70 g, 30.0 mmol) were added. After stirring at room temperature for ca. 5 d, the reaction mixture was concentrated and dried under vacuum to yield 2.93 g (52%) of the target compound, containing ca. 13 wt % of THF.

$^1$H-NMR: 4.71 (t, J=5.6, 1H), 4.61 (t, J=6.1, 1H), 4.44 (t, J=6.3, 1H), 3.74 (t, J=6.9, 1H), 3.49-3.18 (m, 8H), 2.82-2.68 (br. m, 1H).

$^{13}$C-NMR: 97.86, 67.48, 62.82, 62.59, 61.13, 58.84.

(f) Synthesis of (±)-2,2'-(ethane-1,2-diylbis(2-methyloxazolidine-2,3-diyl))bis(ethan-1-ol) (Multi-Alcohol 7)

2,2'-Azanediylbis(ethan-1-ol) (4.2 g, 39.9 mmol) was added to a solution of 2,5-hexanedione (1.17 g, 10.3 mmol) in toluene (50 mL). The reaction mixture was heated under reflux overnight in a Dean-Stark apparatus. After cooling to room temperature on a cold water bath, a biphasic mixture was obtained. The toluene layer was decanted and centrifuged. Concentration and repetitive bulb-to-bulb distillation (0.011 mbar at room temperature and at 50° C.) to remove the remaining toluene afforded 1.70 g of the target compound as a mixture of diastereoisomers, together with some mono-reaction product and remaining 2,2'-azanediylbis (ethan-1-ol).

$^1$H-NMR: 4.50-4.38 (m, 2H), 3.80-3.73 (m, 2H), 3.64 (q, J=7.5, 2H), 3.50-3.40 (m, 4H), 3.11-3.04 (m, 2H), 2.69 (q, J=7.9, 2H), 2.59-2.51 (m, 2H), 2.39-2.31 (m, 2H), 1.67-1.54 (m, 2H), 1.47-1.35 (m, 2H), 0.99 (s, 6H).

$^{13}$C-NMR: 95.15, 95.12, 63.35, 60.54, 60.52, 50.88, 69.64, 49.63, 30.98, 30.67, 19.97, 19.82.

(g) Synthesis of (±)-2,2'-(1,4-phenylenebis(oxazolidine-2,3-diyl))bis(ethan-1-ol) (Multi-Alcohol 8)

Terephthalaldehyde (4.11 g, 30.0 mmol) was dissolved in toluene (75 mL). Then 2,2'-azanediylbis(ethan-1-ol) (7.01 g, 66.0 mmol) and 4-methylbenzenesulfonic acid monohydrate (0.29 g, 1.5 mmol) were added. The mixture was heated under reflux overnight with azeotropic removal of water (Dean-Stark). After cooling to room temperature, a biphasic system was obtained. The toluene layer was decanted, and the oil washed with toluene (25 mL). The oil was dissolved in hot 2-propanol (10 mL), left cooling to room temperature and kept in the fridge. After a few days, crystals were formed, which were washed with cold 2-propanol, dissolved in methanol concentrated and dried under vacuum to give a white solid. Recrystallization with 2-propanol (15 mL), cooling to room temperature and keeping in the fridge afforded 2.55 g of white crystals. The toluene decanted after the reaction was concentrated to give an oil. The oil was dissolved in hot 2-propanol (5 mL), left cooling to room temperature and kept in the fridge to give another 1.07 g of white crystals as a mixture of diastereoisomers. A total of 3.62 g (39%) of the target compound was obtained.

$^1$H-NMR: 7.40 (s, 4H), 4.85 (2 s, 2H), 4.51-4.44 (m, 2H), 3.93-3.85 (m, 4H), 3.51-3.39 (m, 4H), 3.31-3.23 (m, 2H), 2.71-2.63 (m, 2H), 2.58-2.48 (m, 2H), 2.41-2.32 (m, 2H).

$^{13}$C-NMR: 140.29, 127.25, 127.22, 96.20, 64.65, 64.62, 60.02, 53.97, 53.94, 51.80.

(h) Synthesis of (±)-2,2'-(furan-2,5-diylbis(oxazolidine-2,3-diyl))bis(ethan-1-ol) (Multi-Alcohol 9)

5-(Hydroxymethyl)furan-2-carbaldehyde (5.04 g, 40.0 mmol) was dissolved in DMSO (80 mL). NaBr (1.24 g, 40.0 mmol) was added and the mixture heated at 150° C. for 18 h. After cooling to room temperature, the reaction mixture was taken up in ethyl acetate (100 mL) and washed with water (100 mL, 3×) and a saturated solution of NaCl (100 mL). The water phases were re-extracted with ethyl acetate (100 mL). The organic phases were dried (Na$_2$SO$_4$) and concentrated. Column chromatography (SiO$_2$, heptane/ethyl acetate 7:3) afforded 2.17 g (44%) of furan-2,5-dicarbaldehyde (see for example: C. Laugel et al., ChemCatChem, 2014, 6, 1195-1198).

$^1$H-NMR: 9.82 (s, 2H), 7.68 (s, 2H).
$^{13}$C-NMR: 180.68, 153.65, 122.04.

Furan-2,5-dicarbaldehyde (0.75 g, 6.0 mmol) was dissolved in toluene (50 mL). Then 2,2'-azanediylbis(ethan-1-ol) (1.51 g, 14.4 mmol) and some more toluene were added. After stirring at room temperature for 5 min, the mixture was heated under reflux for 15 h with azeotropic removal of water (Dean-Stark) to give a mixture of a brown solid and a yellow solution. The liquid was decanted, concentrated and dried under vacuum to give 1.38 g of the target compound (77%) as a mixture of diastereoisomers, still containing toluene and some remaining 2,2'-azanediylbis(ethan-1-ol).

$^1$H-NMR: 6.35 (s, 2H), 5.06 (2 s, 2H), 4.54-4.48 (m, 2H), 3.88-3.78 (m, 4H), 3.51-3.41 (m, 4H), 3.26-3.19 (m, 2H), 2.80-2.73 (m, 2H), 2.66-2.59 (m, 2H), 2.52-2.43 (m, 2H).

$^{13}$C-NMR: 153.14, 153.13, 108.47, 108.40, 90.07, 90.05, 64.23, 60.06, 54.82, 54.78, 51.52.

(i) Synthesis of (±)-2,2'-(cyclohexane-1,4-diylbis (oxazolidine-2,3-diyl))bis(ethan-1-ol) (Multi-Alcohol 10)

Cyclohexane-1,4-diyldimethanol (melted, 13.24 g, 90.0 mmol) was dissolved in ethyl acetate (300 mL). Polymer immobilized (2,2,6,6-tetramethylpiperidin-1-yl)oxyl (TEMPO) (PIPO AF 944 974265, 1.0 g, 4.9 mmol), KBr (0.1 g, 0.8 mmol), and KHCO$_3$ (2.25 g, 22.5 mmol) were added. Then an aqueous solution of NaOCl (10%, 165 mL) was added dropwise over 2 h, while keeping the temperature of the reaction at 28-30° C. The biphasic mixture was stirred for 2 h, then the phases were separated. The aqueous layer was extracted with ethyl acetate (150 mL) and the combined organic phases washed with a saturated aqueous solution of NaCl (150 mL), a saturated aqueous solution of NaHCO$_3$ (2×) and again with a saturated aqueous solution of NaCl (150 mL), dried (Na$_2$SO$_4$) and concentrated to give 4.12 g (33%) of cyclohexane-1,4-dicarbaldehyde as a mixture of cis/trans isomers (major/minor ca. 3:1), with the spectroscopic data being assigned as follows.

$^1$H-NMR (CDCl$_3$, major): 9.63 (s, 2H), 2.42-2.32 (m, 2H), 2.16-2.07 (m, 2H), 1.87-1.69 (4H), 1.43-1.30 (m, 2H).

$^1$H-NMR (CDCl$_3$, minor): 9.65 (s, 2H), 2.29-2.19 (m, 2H), 1.87-1.69 (m, 8H).

$^{13}$C-NMR (CDCl$_3$, major): 204.12, 47.80, 23.12.
$^{13}$C-NMR (CDCl$_3$, minor): 203.65, 49.47, 24.75.

Cyclohexane-1,4-dicarbaldehyde (1.00 g, 7.2 mmol) was dissolved in toluene (25 mL). Then 2,2'-azanediylbis(ethan-1-ol) (1.82 g, 17.3 mmol) was added. The mixture was heated under reflux for 20 h with azeotropic removal of water (Dean-Stark). After cooling to room temperature, a biphasic mixture was obtained. The toluene was decanted, concentrated and dried under vacuum to give an oil. The oil was taken up in ethanol and kept in the freezer. Concentration of the ethanol finally afforded crystals. Pipetting the supernatant and washing the residue with cold ethanol afforded 0.88 g (12%) of the target compound as a mixture of diastereoisomers.

$^1$H-NMR: 4.44 (br. m, 2H), 3.84-3.79 (m, 2H), 3.70-3.57 (m, 4H), 3.51-3.41 (m, 4H), 3.07 and 3.05 (t, J=6.1, 2H), 2.66-2.54 (m, 4H), 2.43-2.34 (m, 2H), 1.85-1.74 (m, 2H), 1.73-1.62 (m, 2H), 1.30-1.16 (m, 2H), 1.04-0.85 (m, 4H).

$^{13}$C-NMR: 100.01, 99.99, 63.53, 63.50, 60.43, 56.33, 56.31, 52.19, 41.05, 28.36, 28.09, 26.35, 26.02.

(j) Synthesis of (±)-2,2'-(1,9-dioxa-4,12-diazadispiro[4.2.48.25]tetradecane-4,12-diyl)bis(ethan-1-ol) (Multi-Alcohol 11)

Cyclohexane-1,4-dione (2.86 g, 25.0 mmol) was dissolved in toluene (50 mL). After stirring at room temperature for 10 min 2,2'-azanediylbis(ethan-1-ol) (7.96 g, 75.0 mmol) was added. The mixture was stirred for 5 min at room temperature, heated under reflux for 3 h with azeotropic removal of water (Dean-Stark) and left stirring at room temperature overnight. The formation of crystals was observed. The toluene was decanted, and the residue dissolved in hot ethanol (50 mL). After cooling to room temperature, the product was placed in the fridge, then in the freezer to crystallise. Filtration and washing of the residue with ice-cold ethanol gave 4.20 g of crystals. The mother liquor was concentrated and placed in the fridge to recrystallize. After filtration another 1.56 g of crystals were recovered. A total of 5.76 g (80%) of the target compound was obtained.

$^1$H-NMR: 4.40 (t, J=5.6, 2H), 3.74 (t, J=6.6, 4H), 3.45 (q, J=6.2, 4H), 2.92 (t, J=6.6, 4H), 2.49 (t, J=6.6, 4H), 1.68-1.57 (m, 4H), 1.42-1.32 (m, 4H).
$^{13}$C-NMR: 93.69, 62.77, 60.58, 50.99, 49.81, 28.27.

(k) Synthesis of (±)-(1,4-phenylenebis(oxazolidine-2,4,4-triyl))tetramethanol (Multi-Alcohol 12)

2-Amino-2-(hydroxymethyl)propane-1,3-diol (4.86 g, 40.0 mmol) was suspended in ethanol (90 mL). Then terephthalaldehyde (2.74 g, 20.0 mmol) was added and the mixture was heated at reflux for 16 h. Concentration and drying under vacuum gave a white crystalline solid. Dissolving in hot ethanol (30 mL), cooling to room temperature and keeping in the fridge afforded white crystals, which were filtered, washed with cold ethanol and dried under vacuum to give 4.19 g (62%) of the target compound as a mixture of diastereoisomers together with a small amount of (((1E,1'E)-1,4-phenylenebis(methanylylidene))bis(azanylylidene))bis(2-(hydroxymethyl)propane-1,3-diol) (ca. 10%).

$^1$H-NMR: 7.42 (s, 4H), 5.35 (d, J=9.5, 2H), 4.84 (t, J=5.6, 2H), 4.71 (t, J=5.5, 2H), 3.74-3.57 (m, 4H), 3.50-3.37 (m, 8H), 2.79-2.67 (m, 2H).
$^{13}$C-NMR: 140.21, 126.02, 91.25, 91.23, 68.85, 67.19, 63.04, 62.24.

(l) Synthesis of (±)-(1,9-dioxa-4,12-diazadispiro[4.2.4⁸.2⁵]tetradecane-3,3,11,11-tetrayl)tetramethanol (Multi-Alcohol 13)

Cyclohexane-1,4-dione (3.96 g, 34.6 mmol) was dissolved in toluene (90 mL). Then 2-amino-2-(hydroxymethyl)propane-1,3-diol (7.27 g, 59.9 mmol) and 4-methylbenzenesulfonic acid monohydrate (0.1 g, 0.5 mmol) were added. The mixture was heated under reflux for 16 h with azeotropic removal of water (Dean-Stark) to give a white suspension. The suspension was stirred at room temperature for 1 h and filtered. The solid was washed with toluene (20 mL) and dried under vacuum in a desiccator to yield 9.46 g (99%) of the target compound.

$^1$H-NMR: 4.60 (t, J=5.6, 4H), 3.57 (s, 4H), 3.36-3.26 (m, 8H), 2.41 (br. s, 2H), 1.63-1.52 (m, 8H).
$^{13}$C-NMR: 94.19, 67.93, 66.17, 63.46, 34.52.

(m) Synthesis of (±)-(1,9-dioxa-4,12-diazadispiro[4.2.4⁸.2⁵]tetradecane-3,11-diyl)dimethanol (Multi-Alcohol 14)

Cyclohexane-1,4-dione (2.28 g, 19.9 mmol) was dissolved in toluene (50 mL). Then 2-aminopropane-1,3-diol (5.58 g, 60.0 mmol) was added. The mixture was heated under reflux overnight with azeotropic removal of water (Dean-Stark). The formation of a precipitate was observed. After cooling to room temperature, the solvent was decanted, the residue washed with toluene and dissolved in hot ethanol (30 mL). After cooling to room temperature and keeping in the fridge, crystals were formed. Filtration and washing with ice-cold ethanol yielded 3.87 g (75%) of the target compound.

$^1$H-NMR: 4.68 (t, J=5.5, 2H), 3.70 (t, J=7.1, 2H), 3.50-3.25 (m, 8H), 2.41 (br. s, 2H), 1.69-1.45 (m, 8H).
$^{13}$C-NMR: 94.93, 66.36, 61.34, 58.59, 33.97, 32.58.

(n) Synthesis of (±)-(3,11-dimethyl-1,9-dioxa-4,12-diazadispiro[4.2.4⁸.2⁵]tetradecane-3,11-diyl)dimethanol (Multi-Alcohol 15)

Cyclohexane-1,4-dione (4.00 g, 35.0 mmol) was dissolved in toluene (90 mL). Then 2-amino-2-methylpropane-1,3-diol (6.31 g, 60.0 mmol) and 4-methylbenzenesulfonic acid monohydrate (0.1 g, 0.5 mmol) were added. The mixture was heated under reflux for 16 h with azeotropic removal of water (Dean-Stark) to give a mixture of a brown solid and a pale-yellow solution. The liquid was decanted cooled to room temperature to form a white precipitate. The suspension was stirred at room temperature for 1 h and filtered. The solid was washed with toluene (20 mL) and pentane (20 mL) and dried under vacuum in a desiccator to yield 5.74 g (67%) of the target compound as a mixture of diastereoisomers in a ratio of ca. 2:1.

$^1$H-NMR (400 MHz): 4.76-4.68 (m, 2H), 3.69-3.63 (m, 2H), 3.37-3.28 (m, 2H), 3.28-3.09 (m, 4H), 2.33 (br. s, 2H), 1.71-1.45 (m, 8H), 1.07 (2 s, 6H).
$^{13}$C-NMR (100.6 MHz, major isomer): 94.33, 71.47, 66.48, 62.03, 34.87, 34.80, 34.43, 34.37, 23.58, 23.55 or 23.53.
$^{13}$C-NMR (100.6 MHz, minor isomer): 94.67, 71.43, 66.48, 62.22, 35.07, 35.00, 34.65, 34.57, 23.58, 23.55 or 23.53.

(o) Synthesis of (±)-(1,4-phenylenebis(4-ethyloxazolidine-2,4-diyl))dimethanol (Multi-Alcohol 16)

Terephthalaldehyde (2.74 g, 20.0 mmol) was dissolved in ethanol (90 mL) at 50° C. Then 2-amino-2-ethylpropane-1,3-diol (4.91 g, 40.0 mmol) was added. The mixture was stirred at room temperature for several days. Concentration and drying under vacuum gave a viscous, slightly yellow oil that slowly crystallised and that consisted of the target compound and 2,2'-(((1E,1'E)-1,4-phenylenebis(methanylylidene))bis(azanylylidene))-bis(2-ethylpropane-1,3-diol) in a ratio of ca. 4:1 as a mixture of diastereoisomers.

(p) Synthesis of (±)-(3,11-diethyl-1,9-dioxa-4,12-diazadispiro[4.2.4⁸.2⁵]tetradecane-3,11-diyl)dimethanol (Multi-Alcohol 17)

Cyclohexane-1,4-dione (3.96 g, 34.6 mmol) was dissolved in toluene (90 mL). Then 2-amino-2-ethylpropane-1,3-diol (7.34 g, 59.7 mmol) and 4-methylbenzenesulfonic acid monohydrate (0.1 g, 0.5 mmol) were added. The mixture was heated under reflux for 16 h with azeotropic removal of water (Dean-Stark) to give a mixture of a brown solid and a brown solution. The liquid was decanted cooled to room temperature to form a beige precipitate. The suspension was stirred at room temperature for 1 h and filtered. The solid was washed with toluene (20 mL) and dried under vacuum in a desiccator to yield 2.58 g of white crystals. The mother liquor was concentrated, re-dissolved in ethanol (10 mL) and left crystallizing to afford another 1.01 g of crystals. A total of 3.59 g (38%) of the target compound was obtained.

¹H-NMR: 4.65 (t, J=5.5, 2H), 3.62 (d, J=8.3, 2H), 3.38 (d, J=8.3, 2H), 3.27-3.17 (m, 4H), 2.19 (s, 2H), 1.63-1.52 (m, 8H), 1.51-1.36 (m, 4H), 0.81 (t, J=7.5, 6H).
¹³C-NMR: 94.12, 70.46, 64.83, 63.98, 34.68, 34.33, 28.16, 8.38.

(q) Synthesis of 2,2'-(((1E,1'E)-1,4-phenylenebis (methanylylidene))bis(azanylylidene))bis(propane-1, 3-diol) (Multi-Alcohol 18)

2-Aminopropane-1,3-diol (3.72 g, 40.0 mmol) was dissolved in ethanol (90 mL). Then terephthalaldehyde (2.74 g, 20.0 mmol) and ethanol (60 mL) were added. The mixture was heated under reflux for 19 h to afford a white suspension. Cooling to room temperature, filtering, washing with ethanol (15 mL), and drying under vacuum afforded 4.95 g (88%) of the target compound.
¹H-NMR: 8.33 (s, 2H), 7.81 (s, 4H), 4.58 (t, J=5.6, 4H), 3.64 (quint., J=5.3, 4H), 3.47-3.40 (m, 4H), 3.37-3.29 (m, 2H).
¹³C-NMR: 160.47, 137.78, 128.03, 74.81, 62.16.

(r) Synthesis of 2,2'-(((1E,1'E)-furan-2,5-diylbis (methanylylidene))bis(azanylylidene))bis(propane-1, 3-diol) (Multi-Alcohol 19)

2-Aminopropane-1,3-diol (3.72 g, 40.0 mmol) was dissolved in ethanol (150 mL). Then furan-2,5-dicarbaldehyde (2.48 g, 20.0 mmol, prepared as described in Example 1h) was added. The mixture was heated under reflux for 16 h to afford an orange solution. After cooling to room temperature, the product crystallized. Cooling with an ice bath, filtering and washing with cold ethanol (20 mL) afforded 3.97 g, concentration of the filtrate afforded another 1.42 g of the product. A total of 5.39 g (99%) of the target compound was obtained.
¹H-NMR: 8.13 (s, 2H), 7.01 (s, 2H), 4.60 (t, J=5.8, 4H), 3.65-3.57 (m, 4H), 3.45-3.37 (m, 4H), 3.30-3.22 (m, 2H).
¹³C-NMR: 152.26, 149.79, 115.87, 75.03, 62.05.

(s) Synthesis of 2-hydroxyethyl 3-((2-hydroxyethyl) thio)propanoate (Multi-Alcohol 20)

In a dry apparatus under nitrogen, 2-mercaptoethanol (9.3 mL. 132.0 mmol) and 1,8-diazabicyclo[5.4.0]undec-7-ene (DBU, 0.1 mL, 120.0 mmol) were added to dry THF (150 mL). After cooling to 0-5° C. with an ice bath, 2-hydroxyethyl acrylate (13.93 g, 120.0 mmol) was added dropwise during 20 min to the stirred solution. After rinsing with THF (15 mL), the reaction mixture was stirred on the ice bath for 3 h, then at room temperature overnight. Then the reaction mixture was concentrated, poured into an aqueous solution of HCl (1%) and extracted with ethyl acetate (100 mL, 2×). The organic layers were washed with water (50 mL, 2×) and a saturated aqueous solution of NaCl (50 mL). The combined organic layers were dried (Na₂SO₄) and concentrated to afford 6.11 g of crude product.
Then the aqueous layers were extracted with ethyl acetate, saturated with NaCl and re-extracted with ethyl acetate (100 mL). Drying (Na₂SO₄) and concentrating afforded 7.59 g of crude product. Column chromatography of the second part of the product (SiO₂, ethyl acetate/ethanol 19:1) afforded 3.13 g of the target compound.
¹H-NMR (CDCl₃): 4.28-4.24 (m, 2H), 3.86-3.81 (m, 2H), 3.76 (t, J=6.0, 2H), 2.89 (br. S, 2H), 2.85 (t, J=7.1, 2H), 2.75 (t, J=6.0, 2H), 2.69 (t, J=6.9, 2H).
¹³C-NMR (CDCl₃): 172.27, 66.31, 60.87, 60.78, 35.23, 34.83, 26.92.

(t) Synthesis of 2-ethyl-2-(((3-((2-hydroxyethyl) thio)propanoyl)oxy)methyl)propane-1,3-diylbis(3-((2-hydroxyethyl)thio)propanoate) (Multi-Alcohol 21)

In a dry apparatus under nitrogen, 2-mercaptoethanol (16.0 mL. 228.0 mmol) and DBU (0.1 mL, 120.0 mmol) were added to dry THF (150 mL). After cooling to 0-5° C. with an ice bath, 2-((acryloyloxy)methyl)-2-ethylpropane-1,3-diyl diacrylate (trimethylolpropane triacrylate, 22.00 g, 74.2 mmol) was added dropwise during 20 min to the stirred solution.
After rinsing with THF (15 mL), the reaction mixture was stirred on the ice bath for 3 h, then at room temperature overnight. Then the reaction mixture was concentrated, poured into an aqueous solution of HCl (1%) and extracted with ethyl acetate (100 mL, 2×). The organic layers were washed with water (50 mL, 2×) and a saturated aqueous solution of NaCl (50 mL). The combined organic layers were dried (Na₂SO₄) and concentrated to afford 39.43 g (quant.) of the target compound.
¹H-NMR (CDCl₃): 4.09 (s, 6H), 3.76 (t, J=5.9, 6H), 2.82 (t, J=7.1, 6H), 2.74 (t, J=5.9, 6H), 2.65 (t, J=6.9, 6H), 1.51 (q, J=7.6, 2H), 0.91 (t, J=7.6, 3H).
¹³C-NMR (CDCl₃): 171.71, 63.96, 60.82, 40.85, 35.40, 34.76, 26.84, 23.01, 7.38.

(u) Synthesis of 4-hydroxybutyl 3-((1,3-dihydroxypropan-2-yl)amino)propanoate (Multi-Alcohol 22)

2-Aminopropane-1,3-diol (1.86 g, 20.0 mmol) was added to solution of 4-hydroxybutyl acrylate (2.97 g, 20.0 mmol) in acetonitrile (250 mL). The reaction mixture was stirred at room temperature for several days. Concentrating the reaction mixture (0.4 mbar, 45° C.) afforded 4.75 g (quant.) of the target compound, together with some remaining starting material.
¹H-NMR: 4.42 (br. s, 1H), 4.35 (br. s, 2H), 4.01 (t, J=6.7, 2H), 3.40 (t, J=6.3, 2H), 3.38-3.25 (m, 4H), 2.79 (t, J=6.7, 2H), 2.52-2.45 (m, 1H), 2.40 (t, J=6.8, 2H), 1.68-1.55 (m, 2H), 1.50-1.40 (m, 2H).
¹³C-NMR: 172.12, 63.63, 61.06, 60.79, 60.17, 42.74, 34.99, 28.76, 24.88.

(v) Synthesis of bis(2-hydroxyethyl) 3,3'-(butylazanediyl)dipropionate (Multi-Alcohol 23)

Butan-1-amine (2.52 g, 34.5 mmol) in acetonitrile (10 g) was added dropwise during 1 h to a solution of 2-hydroxyethyl acrylate (8.00 g, 69.0 mmol) in acetonitrile (28 g) at 0° C. After stirring overnight at room temperature, the solvent was evaporated. Column chromatography (SiO₂, ethyl acetate) afforded 5.60 g of the target compound, together with some partially hydrolysed product and ethane-1,2-diol.
¹H-NMR (CD₃OD): 4.82 (br. s, 2H), 4.16-4.11 (m, 4H), 3.75-3.70 (m, 4H), 2.79 (t, J=7.1, 4H), 2.50 (t, J=7.1, 4H), 2.49-2.40 (m, 2H), 1.48-1.39 (m, 2H), 1.35-1.26 (m, 2H), 0.92 (t, J=7.4, 3H).
¹³C-NMR (CD₃OD): 174.30, 66.95, 61.01, 54.58, 50.22, 33.10, 30.15, 21.59, 14.38.

(w) Synthesis of bis(2-hydroxyethyl) 3,3'-((4-hydroxybutyl)azanediyl)dipropionate (Multi-Alcohol 24)

4-Amino-1-butanol (3.06 g, 34.3 mmol) in acetonitrile (10 g) was added dropwise during 45 min to a solution of 2-hydroxyethyl acrylate (8.02 g, 69.1 mmol) in acetonitrile (27 g) at 0° C. After stirring overnight at room temperature, the solvent was evaporated. Column chromatography (SiO$_2$, ethyl acetate/ethanol 4:1) afforded 9.25 g of the target compound, together with some partially hydrolysed product and ethane-1,2-diol.

$^1$H-NMR (CD$_3$OD): 4.82 (br. s, 3H), 4.17-4.11 (m, 4H), 3.75-3.70 (m, 4H), 3.57-3.51 (m, 2H), 2.80 (t, J=7.1, 4H), 2.52 (t, J=6.9, 4H), 2.50-2.44 (m, 2H), 1.57-1.49 (m, 4H).

$^{13}$C-NMR (CD$_3$OD): 174.29, 67.00, 62.88, 61.02, 54.72, 50.17, 33.04, 31.61, 24.65.

(x) Synthesis of bis(2-hydroxyethyl) 3,3'-(piperazine-1,4-diyl)dipropionate (Multi-Alcohol 25)

A solution of 2-hydroxyethyl acrylate (8.30 g, 71.5 mmol), piperazine (3.08 g, 35.8 mmol) in acetonitrile (35.9 g) was stirred at room temperature for 4 h. A precipitate was formed, which was filtered, washed with fresh acetonitrile and dried under vacuum to give 9.15 g of the target compound, together with some partially hydrolysed product and ethane-1,2-diol.

$^1$H-NMR (CD$_3$OD): 4.83 (br. s, 2H), 4.18-4.13 (m, 4H), 3.74-3.69 (m, 4H), 2.70 (t, J=7.2, 4H), 2.60-2.45 (br. m, 8H), 2.56 (t, J=7.2, 4H).

$^{13}$C-NMR (CD$_3$OD): 173.89, 67.00, 61.01, 54.50, 53.56, 32.70.

(y) Synthesis of tetrakis(2-hydroxyethyl) 3,3',3'',3'''-(propane-1,3-diylbis(azanetriyl))tetrapropionate (Multi-Alcohol 26)

1,3-Diaminopropane (1.44 g, 19.4 mmol) in acetonitrile (9 g) was added dropwise during 45 min to a solution of 2-hydroxyethyl acrylate (9.02 g, 77.7 mmol) in acetonitrile (30 g) at 0° C. After stirring overnight at room temperature, the solvent was evaporated. Column chromatography (SiO$_2$, ethyl acetate/ethanol 4:1) afforded 11.40 g of the target compound, together with some partially hydrolysed product and ethane-1,2-diol.

$^1$H-NMR (CD$_3$OD): 4.82 (br. s, 4H), 4.17-4.12 (m, 8H), 3.75-3.70 (m, 8H), 2.78 (t, J=7.0, 8H), 2.51 (t, J=6.9, 8H), 2.50-2.42 (m, 4H), 1.66-1.55 (m, 2H).

$^{13}$C-NMR (CD$_3$OD): 174.35, 66.98, 61.03, 52.75, 50.25, 33.16, 25.33.

(z) Synthesis of bis(3-hydroxy-2-(hydroxymethyl)-2-methylpropyl) 3,3'-disulfanediyldipropionate (Multi-Alcohol 27)

A solution of 3-(2-carboxyethyldisulfanyl)propanoic acid (10.73 g, 50.0 mmol), 1,1,1-tris(hydroxymethyl)ethane (18.39 g, 150.0 mmol) and toluene-4-sulfonic acid monohydrate (0.30 g, 1.7 mmol) in toluene (125 mL) was heated under reflux in a Dean-Stark apparatus for 24 h. After cooling to room temperature, a heterogeneous mixture was obtained. The toluene layer was decanted and the remaining solid taken up in ethyl acetate (100 mL) and stirred for 30 min at 0° C. The solid was filtered off and washed with cold ethyl acetate (25 mL), and the filtrate concentrated to afford 18.75 g of the crude compound. Column chromatography (SiO$_2$, ethyl acetate/ethanol 95:5) and drying under high vacuum (0.06 mbar, under gentle heating) afforded 11.41 g (55%) of the target compound.

$^1$H-NMR: 4.48-4.42 (m, 4H), 3.90 (s, 4H), 3.26 (t, J=4.8, 4H), 2.92 (t, J=6.9, 4H), 2.75-2.68 (m, 4H), 1.99 (s, 2H), 1.18 (t, J=7.1, 2H), 0.79 (s, 6H).

$^{13}$C-NMR: 171.06, 66.29, 63.35, 40.49, 33.42, 32.66, 16.37.

(aa) Synthesis of (±)-tetrakis(2-hydroxyethyl) 2,2'-disulfanediyldisuccinate (Multi-Alcohol 28)

Ferrous sulfate hydrate (FeSO$_4$×7 H$_2$O, 80 mg, 0.3 mmol) was added to a stirred solution of 2-mercaptosuccinic acid (29.6 g, 197.1 mmol) in water (250 mL). Then hydrogen peroxide (35%, 14.59 g, 150.1 mmol) was added dropwise during 5-10 min, while maintaining the temperature below 35° C. with an ice bath. After stirring at room temperature overnight, the reaction mixture was extracted with ethyl acetate (250 mL, 3×). The aqueous layer was re-extracted with ethyl acetate (250 mL) and the combined organic layers were washed with a saturated aqueous solution of NaCl (100 mL, 2×), dried (Na$_2$SO$_4$) and concentrated (45° C., 5 mbar) to give 23.40 g of a solid. The solid (22.38 g) was grinded and dried in a desiccator (0.06 mbar) to afford 22.10 g (79%) of 2,2'-disulfanediyldisuccinic acid as a mixture of diastereoisomers.

$^1$H-NMR: 12.69 (br. s, 4H), 3.81-3.73 (m, 2H), 2.85 and 2.82 (dd, J=9.6, 3.5, 2H), 2.71 (dd, J=17.0, 4.8, 2H).

$^{13}$C-NMR: 171.45, 171.38, 171.27, 47.94, 47.35, 35.83, 35.59.

A mixture of 2,2'-disulfanediyldisuccinic acid (1.00 g, 3.4 mmol) and toluene-4-sulfonic acid monohydrate (0.05 g, 0.3 mmol) in ethane-1,2-diol (25 mL) was heated at 120° C. in a Dean-Stark apparatus overnight. Bulb-to-bulb distillation (0.067 mbar, 130° C.) to remove the excess of ethane-1,2-diol afforded 1.78 g of the crude product, which was taken up in ethyl acetate (20 mL) and washed with a saturated aqueous solution of NaHCO$_3$ (5 mL). The aqueous phase was re-extracted with ethyl acetate (25 mL), and the combined organic layers were dried (Na$_2$SO$_4$), concentrated and dried under vacuum 0.087 mbar to afford 1.04 g of the target compound as a mixture of diastereoisomers.

$^1$H-NMR: 4.85-4.76 (m, 4H), 4.14-3.91 (3 m, 10H), 3.62-3.52 (2 m, 8H), 3.05-2.95 (m, 2H), 2.90-2.82 (m, 2H).

$^{13}$C-NMR: 169.96, 169.88, 169.84, 66.83, 66.80, 66.21, 66.20, 58.70, 58.63, 47.19, 46.96, 35.38, 35.29.

(ab) Synthesis of bis(2-hydroxyethyl) 2,2'-(methylenebis(4,1-phenylene))bis(2-oxoacetate) (Multi-Alcohol 29)

Under nitrogen, a solution of ethyl 2-chloro-2-oxoacetate (41.80 g, 306.2 mmol) in CH$_2$Cl$_2$ (75 mL) was added dropwise during 40 min to a suspension of AlCl$_3$ (40.80 g, 306.0 mmol) of in CH$_2$Cl$_2$ (250 mL) at 2-3° C. After stirring at 2-3° C. for 30 min, a solution of diphenylmethane (16.80 g, 99.9 mmol) in CH$_2$Cl$_2$ (75 mL) was added dropwise during 45 min. The mixture was continued to be stirred at 2-3° C. for 3 h and then left warming to room temperature overnight. The reaction mixture was poured onto ice (200 g), decanted and the organic layer washed with water (200 mL, 3×). The aqueous phase was re-extracted with CH$_2$Cl$_2$ (50 mL), and the combined organic layers dried (Na$_2$SO$_4$) and concentrated to give 35.52 g of crude compound. Column chromatography of 27.77 g (SiO$_2$, n-heptane/ethyl acetate 4:1) yielded 10.05 g (35%) of diethyl 2,2'-(methylenebis(4,1-phenylene))bis(2-oxoacetate).

$^1$H-NMR (CDCl$_3$): 7.98-7.94 (m, 4H), 7.34-7.30 (m, 4H), 4.44 (q, J=7.2, 4H), 4.14 (s, 2H), 1.41 (t, J=7.2, 6H).

$^{13}$C-NMR (CDCl$_3$): 185.83, 163.75, 147.25, 131.02, 130.56, 129.52, 62.36, 42.09, 14.11.

Potassium carbonate (0.50 g) was added to a mixture of diethyl 2,2'-(methylenebis(4,1-phenylene))bis(2-oxoacetate) (10.19 g, 27.7 mmol) and ethane-1,2-diol (75.00 g). The reaction mixture was stirred at 80° C. for 1 h, then left cooling to room temperature and stirred overnight. After diluting with ethyl acetate (150 mL) and water (250 mL), the organic layer was decanted and the aqueous phase extracted with ethyl acetate (100 mL, 2×). The combined organic layers were washed with a saturated aqueous solution of NaCl (100 mL, 3×), dried (Na$_2$SO$_4$) and concentrated. Bulb-to-bulb distillation (70° C., 0.057 mbar) to remove remaining volatile compounds afforded 8.00 g (72%) of the target compound.

$^1$H-NMR (CDCl$_3$): 7.98-7.92 (m, 4H), 7.30-7.25 (m, 4H), 4.51-4.44 (m, 4H), 4.08 (s, 2H), 3.95-3.89 (m, 4H), 3.05 (br. s, 2H).

$^{13}$C-NMR (CDCl$_3$): 185.55, 163.43, 147.46, 130.78, 130.72, 129.54, 67.50, 60.40, 42.05.

(ac) Synthesis of bis(2,2-bis(hydroxymethyl)butyl) 2,2'-(methylenebis(4,1-phenylene))bis(2-oxoacetate) (Multi-Alcohol 30)

Potassium carbonate (0.05 g) was added to a mixture of diethyl 2,2'-(methylenebis(4,1-phenylene))bis(2-oxoacetate) (1.00 g, 2.7 mmol, prepared as described in Example lab) and 2-ethyl-2-(hydroxymethyl)propane-1,3-diol (5.00 g). The reaction mixture was stirred at 80° C. for 20 h and, after cooling to room temperature, diluted with methyl tert-butyl ether (MTBE) and water. The aqueous phase was decanted and re-extracted with MTBE (50 mL). The organic layer was washed with water (25 mL, 3×) and a saturated aqueous solution of NaCl (25 mL). The combined organic layers were dried (Na$_2$SO$_4$) and concentrated to give 1.11 g (74%) of the target compound.

$^1$H-NMR: 7.96-7.91 (m, 4H), 7.56-7.50 (m, 4H), 4.57 (t, J=5.1, 4H), 4.25 (s, 4H), 4.23 (s, 2H), 3.33-3.26 (m, 8H), 1.31 (q, J=7.5, 4H), 0.83 (t, J=7.5, 6H).

$^{13}$C-NMR: 186.84, 164.37, 148.80, 130.65, 130.59, 130.28, 66.74, 61.05, 43.24, 41.39, 22.05, 7.77.

(ad) Synthesis of bis(2-hydroxyethyl) 2,2'-(ethane-1,2-diylbis(4,1-phenylene))bis(2-oxoacetate) (Multi-Alcohol 31)

Under nitrogen, a solution of ethyl 2-chloro-2-oxoacetate (41.80 g, 306.2 mmol) in CH$_2$Cl$_2$ (75 mL) was added dropwise during 50 min to a suspension of AlCl$_3$ (40.80 g, 306.0 mmol) of in CH$_2$Cl$_2$ (250 mL) at 2-3° C. After stirring at 2-3° C. for 30 min, a solution of 1,2-diphenylethane (18.60 g, 100.0 mmol) in CH$_2$Cl$_2$ (75 mL) was added dropwise during 45 min. The mixture was continued to be stirred at 2-3° C. for 1 h and at room temperature for 4 h. The reaction mixture was slowly poured onto ice (200 g), diluted with CH$_2$Cl$_2$ (100 mL), decanted and the organic layer washed with water (150 mL, 3×). The aqueous phase was re-extracted with CH$_2$Cl$_2$ (50 mL), and the combined organic layers dried (Na$_2$SO$_4$) and concentrated to afford 39.22 g of the crude compound as a pale yellow-greenish solid. Repetitive recrystallization with acetone at −20° C. (2×) and with n-heptane/diethyl ether (2:1) at room temperature afford a total of 22.69 g (59%) of diethyl 2,2'-(ethane-1,2-diylbis(4,1-phenylene))bis(2-oxoacetate).

$^1$H-NMR (CDCl$_3$): 7.95-7.90 (m, 4H), 7.31-7.25 (m, 4H), 4.45 (q, J=7.1, 4H), 3.04 (s, 4H), 1.42 (t, J=7.2, 6H).

$^{13}$C-NMR (CDCl$_3$): 185.98, 163.90, 148.70, 130.72, 130.35, 129.08, 62.33, 37.27, 14.12. Potassium carbonate (0.25 g) was added to a suspension of diethyl 2,2'-(ethane-1,2-diylbis(4,1-phenylene))bis(2-oxoacetate) (23.01 g, 60.2 mmol) in ethane-1,2-diol (144 g). The reaction mixture was stirred at 80° C. for 20 h. Then more potassium carbonate (0.75 g) was added and the reaction continued to be stirred at 80° C. for 8 h. After cooling to room temperature overnight, a solid product was obtained. The reaction mixture was heated and then diluted with ethyl acetate (150 mL) and water (250 mL). The organic layer was decanted and the aqueous layer extracted with ethyl acetate (100 mL, 2×). The combined organic layers were washed with a saturated aqueous solution of NaCl, dried (Na$_2$SO$_4$) and concentrated to give 22.33 g of the crude product. Recrystallization with acetone (50 mL) in the refrigerator afforded 3.25 g (13%) of the target compound.

$^1$H-NMR (CDCl$_3$): 7.97-7.91 (m, 4H), 7.29-7.23 (m, 4H), 4.53-4.46 (m, 4H), 3.98-3.92 (m, 4H), 3.02 (s, 4H), 2.58 (br. s, 2H).

$^{13}$C-NMR (CDCl$_3$): 185.62, 163.66, 148.85, 130.57, 130.49, 129.14, 67.45, 60.54, 37.25.

(ae) Synthesis of benzene-1,3,5-triyl tris(3-((2-hydroxyethyl)thio)propyl)tricarbonate (Multi-Alcohol 32)

Benzene-1,3,5-triol (7 g, 55.6 mmol) and triethylamine (24 mL, 172 mmol) were dissolved in THF (100 mL) in a 250 mL round-bottomed flask. The temperature of the reaction mixture was cooled with ice and allyl carbonochloridate (18 mL, 169 mmol) was added. A white precipitate was formed and the reaction mixture was stirred at 0° C. for 3 h. The white solid was filtered and the reaction mixture was concentrated under reduced pressure. A colorless oil was obtained and dissolved in ethyl acetate (100 mL). The organic solution was washed with a solution of K$_2$CO$_3$ (at 5%, ×3 100 mL) The organic layer was dried with anhydrous Na$_2$SO$_4$, filtered and concentrated to afford triallyl benzene-1,3,5-triyl tricarbonate.

$^1$H-NMR (CDCl$_3$): 7.05 (s, 3H), 5.98 (qt, 3H), 5.43 (dq, 3H), 5.34 (dq, 3H), 4.73 (dt, 6H).

$^{13}$C-NMR (CDCl$_3$): 152.52, 151.46, 130.81, 119.89, 112.02, 69.49.

This oil (6.0 g, 15.8 mmol) and 2,2-dimethoxy-1,2-diphenylethanone (0.1 g, 0.39 mmol) were dissolved in THF (30 mL) in a 250 mL round-bottomed flask to give a colorless solution. Then 2-mercaptoethanol (3.96 g, 50.7 mmol) was added and the reaction mixture was irradiated under UV-A light at 2 mW/cm$^2$ for 5 h. The reaction mixture was concentrated under reduced pressure, diluted in ethyl acetate (40 mL), washed with a solution of K$_2$CO$_3$ (5% in water, 25 mL×2). The organic layer was dried with anhydrous Na$_2$SO$_4$, filtered and concentrated to afford benzene-1,3,5-triyl tris(3-((2-hydroxyethyl)thio)propyl)tricarbonate.

$^1$H-NMR (CDCl$_3$): 7.05 (s, 3H), 4.37 (t, 6H), 3.75 (q, 6H), 2.74 (t, 6H), 2.66 (t, 6H), 2.48 (t, 3H), 2.03 (quint., 6H).

$^{13}$C-NMR (CDCl$_3$): 152.63, 151.42, 112.04, 67.55, 60.54, 35.15, 28.54, 27.88.

(af) Synthesis of bis(3-((2-hydroxyethyl)thio)propyl) 2-((2-hydroxyethyl)thio)succinate (Multi-Alcohol 33)

In a 100 mL round-bottomed flask, diallyl maleate (3 mL, 16.39 mmol) and triethylamine (0.25 ml, 1.794 mmol) were dissolved in THF (50 mL) to give a colorless solution. 2-Mercaptoethanol (1.4 mL, 19.98 mmol) was added and the reaction mixture was stirred at 0° C. 2,3,4,6,7,8,9,10-Octahydropyrimido[1,2-a]azepine (0.1 mL, 16.39 mmol) was added and the reaction mixture was stirred at room temperature for 5 h, and finally concentrated under reduced pressure to afford diallyl 2-((2-hydroxyethyl)thio)succinate.

$^1$H-NMR (CDCl$_3$): 5.92 (m, 2H), 5.35 (m, 2H), 5.26 (m, 2H), 4.64 (m, 4H), 3.80 (m, 3H), 2.90 (m, 6H)

$^{13}$C-NMR (CDCl$_3$): 171.51, 170.43, 131.61, 118.89, 118.71, 66.16, 65.77, 60.99, 41.16, 36.36, 35.14.

In a 100 mL round-bottomed flask, diallyl 2-((2-hydroxyethyl)thio)succinate (3.5 g, 12.7 mmol) and 2-mercaptoethanol (1.9 mL, 27.1 mmol) were dissolved in THF (50 mL) to give a colorless solution. 2,2-Dimethoxy-1,2-diphenylethanone (0.1 g, 0.39 mmol) was added and the reaction mixture was irradiated under UV-A light at 2 mW/cm$^2$ for 3 h. The reaction mixture was concentrated under reduced pressure and ethyl acetate (50 mL) was added. The organic solution was washed with a solution of K$_2$CO$_3$ (5% in water, 25 mL) and water (25 mL). The organic layer was dried with anhydrous Na$_2$SO$_4$, filtered and concentrated to afford bis (3-((2-hydroxyethyl)thio)propyl) 2-((2-hydroxyethyl)thio) succinate.

$^1$H-NMR (CDCl$_3$): 4.28 (t, 2H), 4.22 (t, 2H), 3.80 (m, 2H), 3.74 (m, 4H), 2.99 (m, 2H), 2.93 (m, 2H), 2.83 (m, 2H), 2.73 (m, 6H), 2.65 (t, 2H), 2.61 (t, 2H), 1.97 (m, 2H), 1.94 (m, 2H).

$^{13}$C-NMR (CDCl$_3$): 171.86, 170.77, 64.00, 63.63, 61.64, 60.67, 60.60, 41.35, 36.46, 35.10, 35.07, 34.88, 28.68, 28.64, 28.09, 28.05.

(ag) Synthesis of bis(3-hydroxy-2-(hydroxymethyl)-2-methylpropyl)carbonate (Multi-Alcohol 34)

1,1,1-Tris(hydroxymethyl)ethane (24.5 g, 200.0 mmol) was suspended in THF (250 mL). Then 2,2-dimethoxypropane (32 mL, 0.84 g mL$^{-1}$, 258.1 mmol) and p-toluenesulfonic acid (50 mg) were added. After stirring for 1 h, K$_2$CO$_3$ (1.0 g) was added and the mixture stirred for 1 h, before being filtered and concentrated under reduced pressure (45° C., 4 mbar). After addition of Primol™ (5.06 g) as ballast, fractional distillation (0.2 mbar, 70° C.) afforded a total of 31.0 g (97%) of (2,2,5-trimethyl-1,3-dioxan-5-yl) methanol as a colorless oil.

$^1$H-NMR (CDCl$_3$): 3.69 (s, 2H), 3.64 (dd, J=35.2, 12.0, 4H), 2.22 (br. s, 1H), 1.44 (s, 3H), 1.40 (s, 3H), 0.83 (s, 3H).

$^{13}$C-NMR (CDCl$_3$): 97.98, 66.34, 65.91, 34.75, 27.30, 20.14, 17.58.

A mixture of (2,2,5-trimethyl-1,3-dioxan-5-yl)methanol (3.88 g, 24.2 mmol), diethyl carbonate (1.20 g, 10.0 mmol) and sodium methylate (11 mg) was heated to 90° C. for 5 h, then at 125° C. overnight. After cooling to room temperature, the product crystallized. Recrystallization in heptane (10 mL, upon heating), filtrating, washing with heptane and drying under vacuum afforded 1.02 g (29%) of bis((2,2,5-trimethyl-1,3-dioxan-5-yl)methyl)carbonate as white crystals.

$^1$H-NMR (CDCl$_3$): 4.23 (s, 4H), 3.65 (dd, J=30.3, 11.9, 8H), 1.44 (s, 6H), 1.40 (s, 6H), 0.87 (s, 6H).

$^{13}$C-NMR (CDCl$_3$): 155.45, 98.09, 70.36, 66.09, 33.68, 27.29, 20.02, 17.60.

A mixture of bis((2,2,5-trimethyl-1,3-dioxan-5-yl) methyl)carbonate (1.00 g, 2.9 mmol) and KHSO$_4$ (33 mg) in methanol (9 mL) and water (1 mL) was stirred at room temperature for 3 h. Then NaHCO$_3$(250 mg) was added and the solvent evaporated. The reaction mixture was taken up in ethyl acetate (20 mL) and washed with a saturated aqueous solution of NaCl (10 mL). The organic layer was dried (Na$_2$SO$_4$), filtered and concentrated.

The product was recrystallized in acetone. After being put in the freezer, the crystals were filtered and washed with a minimum of ice-cold acetone to afford 0.06 g (8%) of the target compound.

$^1$H-NMR (CD$_3$COCD$_3$): 4.11 (s, 4H), 3.76 (t, J=5.4, 4H), 3.49 (t, J=5.3, 8H), 0.89 (s, 6H).

$^{13}$C-NMR (CD$_3$COCD$_3$): 156.51, 70.50, 65.72, 41.73, 16.78.

Example 2

Preparation of Polyurethane Core-Shell Microcapsules Containing Cleavable Multi-Alcohols According to Formula (I) and their Performance to Release Fragrances on Cotton Upon Rubbing (a) Preparation of Perfume 1

Perfume 1 was prepared as an equiponderal mixture of methyl 2,2-dimethyl-6-methylidenecyclohexanecarboxylate (origin: Firmenich SA), 2-tert-butyl-1-cyclohexyl acetate (origin: International Flavors and Fragrances), 4-tert-butyl-1-cyclohexylacetate, 3-(4-isopropylphenyl)-2-methylpropanal and (2Z)-2-phenyl-2-hexenenitrile (origin: Firmenich SA).

(b) Co-Polymerization of Multi-Alcohols with Isocyanates at the Oil-Water Interface To verify the co-polymerization of cleavable multi-alcohols with isocyanates to form polyurethanes in the presence of perfume, membranes were formed in a 2D approach at the interphase between an oil phase on top of a water phase.

Multi-alcohols (1 equiv. of —OH groups) were dissolved in a 1 wt % solution of poly(vinyl alcohol) (PVOH) in water (5 g) together with a precise quantity of sodium citrate (ca. 0.4 equiv.). Commercially available polyisocyanate Takenate© D-110 N (origin: Mitsui Chemicals, 0.33 g, 0.86 mmol; 0.7 equiv. of —NCO groups) was separately dissolved in Perfume 1 (4.7 g) and gently pipetted on top of the aqueous solution in a 30 mL vial. The vial was left non-agitated in a water bath, which was kept at 25° C. during 30 min, heated in four steps to 70° C. during 1 h (40; 50; 60; 70° C.), kept at 70° C. during 2 h, and finally allowed to cool to room temperature.

The membranes formed at the interphase were carefully removed from the polymerization bottle by tweezers. The aqueous phase was carefully transferred to a round bottom flask and frozen on dry ice. All water was removed by freeze drying (Christ Alpha 1-4, Fischer Science), and the resulting powder was characterized by NMR spectroscopy in D$_2$O. The ratio of the average signal of all triplets in the $^{13}$C spectrum of the multi-alcohol compared to that of citrate (triplet peak at 47-49 ppm) was used to calculate the fraction of monomer that was left in the aqueous phase, i.e. that had not reacted with the isocyanate.

The following fractions of cleavable multi-alcohols reacted with the isocyanate and were thus incorporated into the polymer membrane:

|  | Fraction of reacted multi-alcohol [%] |
|---|---|
| Multi-Alcohol 23 | 14 |
| Multi-Alcohol 24 | 6 |
| Multi-Alcohol 25 | 15 |
| Multi-Alcohol 26 | 37 |

The different multi-alcohols were thus successfully incorporated into the 2D membrane by interfacial reaction with a polyisocyanate.

(c) Preparation of Microcapsules 1-3

Sodium citrate (ca. 0.91 g) and one of the multi-alcohols (one equivalent of —OH groups) according to formula (I), prepared as described in Example 1, were dissolved in a 1 wt % solution of PVOH in water (35 g). Takenate® D-110 N-Trimethylol propane-adduct of xylylene diisocyanate, origin: Mitsui Chemicals, Inc., Japan, 75% solution of polyisocyanate in ethyl acetate (3.12 g, 8.2 mmol; 0.7 equiv. of —NCO groups) was dissolved in Perfume 1 (21 g). The oil phase was emulsified in the 1 wt % PVOH solution (35 g) containing the multi-alcohol with an Ultra-Turrax® (IKA 25; highest speed during 3 min). The emulsion was transferred to a reactor, equipped with a mechanical stirrer (RW20, IKA Labortechnik) and a water bath. After 1 h at 25° C., the mixture was heated in four steps to 70° C. during 1 h (40; 50; 60; 70° C.). Water (10 g) was added and the mixture kept at 70° C. during 2 h before being cooled to room temperature to give dispersions of Microcapsules 1-3. Microscope images of the capsules were taken ca. 1 h after removing the water bath (see FIG. 1).

The following core-shell microcapsules were prepared:

|  |  | Amount of multi-alcohol [g] | pH of emulsion |
|---|---|---|---|
| Microcapsule 1 | Multi-Alcohol 23 | 1.75 | 5.53 |
| Microcapsule 2 | Multi-Alcohol 24 | 1.24 | 4.89 |
| Microcapsule 3 | Multi-Alcohol 26 | 1.58 | 5.15 |

As shown in FIG. 1, core-shell microcapsules were formed.

(d) Performance of Fragrance Release on Cotton with and without Rubbing

To demonstrate the release properties of the microcapsules, headspace concentrations of methyl 2,2-dimethyl-6-methylidenecyclohexanecarboxylate were determined for microcapsules deposited on cotton tissue with and without rubbing. The release of methyl 2,2-dimethyl-6-methylidenecyclohexanecarboxylate is considered as being representative for the other perfume molecules of Perfume 1.

Ca. 0.15 g of the dispersions of Microcapsules 1-3 were diluted in ca. 15 g of demineralized water. For each sample, three or four cotton sheets were pre-washed, cut to 12×12 cm², and marked with circle with a diameter of 10 cm. The diluted dispersion of microcapsules (1 mL) was pipetted onto one cotton sheet filling the marked circular area. The sheets were line dried during 1 h, after which they were stored in aluminum foil. The day after, each cotton sheet was left to equilibrate in a 1 L beaker covered with an aluminum foil during 5 min. Then the amount of methyl 2,2-dimethyl-6-methylidenecyclohexanecarboxylate was measured during 2 min by atmospheric pressure chemical ionization mass spectrometry (see for example: O. Viry et al., Food Res. Int., 2018, 109, p. 52-58). The cotton sheet was then manually rubbed 10 times, left to equilibrate in the beaker for another 5 min, and measured again during 2 min. The average intensity of the protonated molar mass ions of the different fragrances (139, 172, 183 and 191 g/mol) recorded over 1 min was subtracted by the background and divided by the concentration of the microcapsules in the diluted dispersion to yield the relative headspace intensity.

The following amounts of methyl 2,2-dimethyl-6-methylidenecyclohexanecarboxylate were released from the microcapsules:

|  | Normalized headspace intensity before rubbing [a.u.] | Normalized headspace intensity after rubbing [a.u.] |
|---|---|---|
| Microcapsule 1 | 185 (±34) | 1316 (±149) |
| Microcapsule 2 | 225 (±62) | 1276 (±166) |
| Microcapsule 3 | 188 (±42) | 1305 (±134) |

Microcapsules 1-3 containing a cleavable multi-alcohol according to formula (I) are thus suitable to encapsulate and deliver fragrances on cotton.

Example 3

Preparation of Polyamide Microcapsules Containing Cleavable Multi-Alcohols of Formula (I)

TABLE 1

| Composition of Perfume 2: | |
|---|---|
| Raw materials | % |
| Ethyl 2-methyl-pentanoate | 3.20 |
| Eucalyptol | 7.80 |
| 2,4-Dimethyl-3-cyclohexene-1-carbaldehyde [1] | 0.75 |
| Decanal | 0.75 |
| Citronellyl nitrile | 4.30 |
| Isobornyl acetate | 3.00 |
| 2-tert-butyl-1-cyclohexyl acetate [2] | 9.80 |
| Citronellyl acetate | 1.30 |
| 2-Methylundecanal | 3.00 |
| Diphenyloxide | 0.80 |
| Dodecanal | 1.30 |
| Dicyclopentadiene acetate | 9.85 |
| beta-Ionone | 3.30 |
| gamma-Undecalactone | 18.75 |
| Hexyl salicylate | 15.90 |
| Benzyl salicylate | 16.20 |
| TOTAL | 100 |

[1] Origin: Firmenich SA, Geneva, Switzerland
[2] Origin and trademark from IFF, USA Preparation of Microcapsule 4 with Multi-Alcohol 1 (Bis(2-hydroxyethyl)disulfide)

In a round bottom flask, trimesoyl chloride (TMCl, 0.18 g) was dissolved in benzyl benzoate (0.5 g). Bis(2-hydroxyethyl)disulfide (0.16 g) was dissolved in benzyl benzoate (5 g) and this solution was added to the first solution and stirred at 60° C. for 10 min (Solution A). Sodium caseinate (1 g) was dispersed in Perfume 2 (25 g). A second solution of TMCl (1.56 g) in benzyl benzoate (2 g) was prepared and added to the perfume dispersion. Solution A was finally added to the dispersion to afford the oil phase. The latter was dispersed in a solution of L-Lysine (2.55 g) in water (95 g) with an Ultra Turrax T25 (S 25 N—10G) at 24,000 rpm for 5 min. A solution of ethylene diamine (EDA, 0.22 g) in water (5 g) was added dropwise over the course of 5 min. The reaction mixture was stirred at 30° C. in an orbital shaker (IKA KS 3000) at 250 rpm for 4 h to afford a white dispersion.

Microcapsule 5 was prepared according to the protocol of Microcapsule 4 with 0.16 g of Multi-Alcohol 1.

Preparation of Microcapsule 6 with Multi-Alcohol 2 (2,2'-disulfanediylbis(propane-1,3-diol))

Microcapsule 6: In a round bottom flask, Bovin Serum Albumin (BSA, 0.95 g) was dispersed in benzyl benzoate (5.00 g) at 60° C. A solution of TMCl (0.88 g) in benzyl benzoate (2.50 g) was added to the BSA dispersion. In another round bottom flask, a solution of Multi-Alcohol 2 (0.38 g) in acetone (5.00 g) was added to a solution of TMCl (0.88 g) in benzyl benzoate (2.50 g) and the reaction mixture was stirred for few minutes. The solution and the dispersion were added to Perfume 2 (25.14 g) at room temperature to afford the oil phase. The latter was dispersed in a solution of L-Lysine (2.50 g) in water (94.05 g) with an Ultra Turrax T25 (S 25 N—10G) at 24,000 rpm for 1 min. A solution of EDA (0.48 g) in water (5.00 g) was added dropwise over the course of 5 min. The reaction mixture was stirred at 30° C. in an orbital shaker (IKA KS 3000) at 250 rpm for 4 h to afford a white dispersion.

Microcapsule 7 was prepared according to the protocol of Microcapsule 6 where the solution of EDA was replaced by a solution of cystamine dihydrochloride (1.8 g) in an aqueous solution of guanidine carbonate (30 wt %, 5.00 g).

Preparation of Microcapsules 8-11 with Multi-Alcohol 3 (3-(2,3-dihydroxypropyldisulfanyl)propane-1,2-diol)

Microcapsule 8: In a round bottom flask, TMCl (0.89 g) was dissolved in benzyl benzoate (2.59 g). Multi-Alcohol 3 (0.55 g) was dissolved in benzyl benzoate (2.51 g) and this solution was added to the first solution, and stirred at 60° C. for 1 h (Solution A). Sodium caseinate (1.94 g) was dispersed in Perfume 2 (24.92 g). A second solution of TMCl (1.76 g) in benzyl benzoate (2.49 g) was prepared and added to the perfume dispersion, then Solution A was added to the dispersion to afford the oil phase. The latter was dispersed in a solution of L-Lysine (2.57 g) in water (94.39 g) with an Ultra Turrax T25 (S 25 N—10G) at 24,000 rpm for 5 min. A solution of EDA (0.24 g) in water (5.30 g) was added dropwise over the course of 5 min. The reaction mixture was stirred at 30° C. in an orbital shaker (IKA KS 3000) at 250 rpm for 4 h to afford a white dispersion.

Microcapsule 9: In a round bottom flask, TMCl (2.63 g) was dissolved in benzyl benzoate (2.53 g). Multi-Alcohol 3 (0.22 g) was dissolved in acetone (2.64 g) and this solution was added to the first solution, and stirred at 60° C. for 1 h (Solution A). Sodium caseinate (1.03 g) was dispersed in benzyle benzoate (5.03 g, Solution B). Solutions A and B were added to Perfume 2 (25.6 g) to afford the oil phase. The latter was dispersed in a solution of L-Lysine (2.56 g) in water (94.27 g) with an Ultra Turrax T25 (S 25 N—10G) at 24,000 rpm for 5 min. A solution of EDA (0.73 g) in water (5.15 g) was added dropwise over the course of 5 min. The reaction mixture was stirred at 30° C. in an orbital shaker (IKA KS 3000) at 250 rpm for 4 h to afford a white dispersion.

Microcapsule 10 was prepared according to the protocol of Microcapsule 8 with 0.31 g of Multi-Alcohol 3.

Microcapsule 11: In a round bottom flask, TMCl (2.68 g) was dissolved in benzyl benzoate (2.62 g). Multi-Alcohol 3 (0.34 g) was dissolved in acetone (2.66 g) and this solution was added to the first solution, and stirred at 60° C. for 1 h (Solution A). Sodium caseinate (0.98 g) was dispersed in benzyl benzoate (5.09 g, Solution B) at 60° C. for 30 min. Solutions A and B were added to Perfume 2 (24.6 g) to afford the oil phase. The latter was dispersed in a solution of L-Lysine (2.49 g) and EDA (0.75 g) in water (95.65 g) with an Ultra Turrax T25 (S 25 N—10G) at 24,000 rpm for 5 min. The reaction mixture was stirred at 30° C. in an orbital shaker (IKA KS 3000) at 250 rpm for 4 h to afford a white dispersion.

Preparation of Microcapsules 12-14 with Multi-Alcohol 8 (2,2'-(1,4-phenylenebis(oxazolidine-2,3-diyl))bis(ethan-1-ol))

Microcapsule 12: In a round bottom flask, a solution of TMCl (0.88 g) in benzyl benzoate (2.50 g) was added to a dispersion of Bovin Serum Albumin (BSA, 0.95 g) in benzyl benzoate (5.00 g) at 60° C. for 10 min. In another round bottom flask, a solution of Multi-Alcohol 8 (1.54 g) in acetone (5.00 g) was added to a solution of TMCl (0.88 g) in benzyl benzoate (2.50 g) and the reaction mixture was stirred for a few minutes. The solution and the dispersion were added to Perfume 2 (25.14 g) at room temperature to afford the oil phase. The latter was dispersed in a solution of L-Lysine (2.50 g) in water (94.05 g) with an Ultra Turrax T25 (S 25 N—10G) at 24,000 rpm for 1 min. A solution of EDA (0.48 g) in water (5.00 g) was added dropwise over the course of 5 min. The reaction mixture was stirred at 30° C. in an orbital shaker (IKA KS 3000) at 250 rpm for 4 h to afford a white dispersion.

Microcapsule 13 was prepared according to the protocol of Microcapsule 12 where the solution of EDA was replaced by a solution of cystamine dihydrochloride (1.8 g) in an aqueous solution of guanidine carbonate (30 wt %, 5.00 g).

Microcapsule 14 was prepared according to the protocol of Microcapsule 12 where the solution of EDA was replaced by a solution of diethylene triamine (0.83 g) in water (5.00 g).

Preparation of Microcapsule 15 with Multi-Alcohol 1 (bis(2-hydroxyethyl)disulfide) in Water and Multi-Alcohol 3 (3-(2,3-dihydroxypropyldisulfanyl)propane-1,2-diol) in Oil In a round bottom flask, TMCl (2.65 g) was dissolved in benzyl benzoate (5.00 g). Multi-Alcohol 3 (1.14 g) was dissolved in acetone (2.60 g). This solution was added to the first solution and stirred at 60° C. for 1 h. The solution was added to Perfume 2 (25 g) to afford the oil phase. The latter was dispersed in aqueous solution of gum Arabic (Senegal, 1 wt %, 95.22 g) with an Ultra Turrax T25 (S 25 N—10G) at 24,000 rpm for 5 min. A solution of Multi-Alcohol 1 (0.78 g) in water (5.00 g) was added dropwise over the course of 5 min. The pH of the emulsion was controlled to a value of 4.0 by adding aqueous solution of sodium bicarbonate (5 wt %, 70.77 g). The reaction mixture was stirred at 90° C. for 4 h to afford a white dispersion.

Preparation of Microcapsule 16-18 with Multi-Alcohol 4 2,2'-(disulfanediylbis(methylene))bis(2-methylpropane-1,3-diol)

In a beaker, sodium caseinate (2 g) was dispersed in Perfume 2 (25 g). The dispersion was stirred at 60° C. for 1 h. In a round bottom flask, TMCl (1.74 g) was dissolved in benzyl benzoate (5.14 g). Multi-Alcohol 4 (0.68 g) was dissolved in acetone (2.49 g) at 40° C. This solution was added to the first solution and stirred at RT for 1 h. The solution was added to Perfume 2 dispersion (25 g) to afford the oil phase. The latter was dispersed in a solution of L-lysine (2.56 g) in water (95 g) with an Ultra Turrax T25 (S 25 N—10G) at 24,000 rpm for 5 min. A solution of ethylene diamine (0.12 g) in water (5.00 g) was added dropwise over the course of 5 min. The reaction mixture was stirred at 30° C. for 4 h to afford a white dispersion.

Microcapsule 17 was prepared according to the protocol of Microcapsule 16 with 0.44 g of Multi-Alcohol 4 and 0.17 g of ethylene diamine.

Microcapsule 18 was prepared according to the protocol of Microcapsule 16 with 0.28 g of Multi-Alcohol 4 and 0.20 g of ethylene diamine.

Example 4

Preparation of Cleavable Polyisocyanates from Cleavable Multi-Alcohols of Formula (I) and Preparation of Core-Shell Microcapsules Thereof
Preparation of Cleavable Polyisocyanates 1-5

Preparation of (((((benzene-1,3,5-triyltris(oxy))tris (carbonyl))tris(oxy))tris (propane-3,1-diyl))tris(sulfanediyl))tris(ethane-2,1-diyl)tris(3-(isocyanato methyl)benzylcarbamate) (Polyisocyanate 1)

1,3-Bis(isocyanatomethyl)benzene (1.55 mL, 9.90 mmol) and tin(II) 2-ethylhexanoate (0.09 g, 0.011 mmol) were introduced under nitrogen in a 50 mL round bottomed three necked flask to give a colorless solution. Benzene-1,3,5-triyl tris(3-((2-hydroxyethyl)thio)propyl)tricarbonate (Multi-Alcohol 32, 2.04 g, 3.33 mmol) in ethyl acetate (4.4 mL) was added dropwise during 5 min. The reaction mixture was stirred for 3 h at 50° C., then the medium was slowly cooled to room temperature under stirring before use.

$^1$H-NMR (CDCl$_3$): 7.39-7.33, 7.28-7.27, 7.22, 7.16, 7.00, 4.53, 4.47, 4.33, 4.25, 2.75, 2.68, 2.04, 2.01.

$^{13}$C-NMR (CDCl$_3$): 156.36, 152.64, 154.39, 137.62, 129.41, 129.19, 127.03, 126.29, 125.84, 125.75, 125.05, 112.05, 67.57, 64.10, 46.30, 44.83, 30.98, 28.40.

Preparation of 2-ethyl-2-(1-(3-(isocyanatomethyl) phenyl)-3,10-dioxo-4,11-dioxa-7-thia-2-azadodecan-12-yl)propane-1,3-diyl bis(3-((2-(((3-(isocyanatomethyl)benzyl)carbamoyl)oxy)-ethyl)thio)propanoate) (Polyisocyanate 2)

1,3-Bis(isocyanatomethyl)benzene (1.4 mL, 8.9 mmol) and tin(II) 2-ethylhexanoate in ethyl acetate (0.09 g, 0.34 mmol) were introduced in a 50 mL round bottomed three necked flask to give a colorless solution. A solution of 2-ethyl-2-(((3-((2-hydroxyethyl)thio)propanoyl)oxy)-methyl)propane-1,3-diyl bis(3-((2-hydroxyethyl)thio)propanoate) (Multi-Alcohol 21, 1.54 g, 2.89 mmol) in ethyl acetate (3.1 mL) was added dropwise. The reaction mixture was stirred at 50° C. for 3 h and then slowly cooled to room temperature under stirring.

$^1$H-NMR (CDCl$_3$):8.74, 7.75, 7.71, 7.42, 7.41, 7.36, 7.34, 7.32, 7.24, 7.21, 7.12, 6.64, 4.62, 4.58, 4.25, 4.21, 4.19, 4.15, 4.08, 4.00, 3.32, 2.73, 2.62, 2.50, 1.42, 0.82.

$^{13}$C-NMR (CDCl$_3$): 170.20, 158.10, 156.13, 141.45, 140.79, 140.24, 139.65, 137.75, 137.22, 137.17, 128.98, 128.54, 128.11, 126.28, 126.11, 125.67, 125.40, 125.35, 125.25, 125.04, 122.76, 63.33, 63.00, 59.16, 45.74, 45.69, 45.57, 43.66, 43.54, 42.89, 42.76, 40.40, 34.22, 29.98, 26.34, 22.31, 13.98, 7.14.

Preparation of 2-ethyl-2-(1-(5-isocyanato-1,3,3-trimethylcyclohexyl)-3,10-dioxo-4,11-dioxa-7-thia-2-azadodecan-12-yl)propane-1,3-diyl bis(3-((2-((((5-isocyanato-1,3,3-trimethylcyclohexyl)-methyl) carbamoyl)oxy)ethyl)thio)propanoate) (Polyisocyanate 3)

5-Isocyanato-1-(isocyanatomethyl)-1,3,3-trimethylcyclohexane (3.1 mL, 14.63 mmol) and tin(II) 2-ethylhexanoate (0.09 g, 0.011 mmol) were introduced in a 50 mL round bottomed three necked flask to give a colorless solution. The reaction mixture was stirred at 50° C. for 5 min. 2-Ethyl-2-(((3-((2-hydroxyethyl)thio) propanoyl)oxy)methyl)propane-1,3-diyl bis(3-((2-hydroxy ethyl)thio)propanoate) (Multi-Alcohol 21, 2.53 g, 4.77 mmol) in ethyl acetate (6.3 mL) was added dropwise over the time of 5 min. The reaction mixture was stirred for 3 h at 50° C., and the reaction product was used without further purification.

$^1$H-NMR (CDCl$_3$): 5.18, 4.90, 4.21, 4.07, 3.81, 3.65, 3.06, 3.03, 2.94, 2.83, 2.77, 2.65, 1.91, 1.84, 1.81, 1.74, 1.51, 1.25, 0.80.

$^{13}$C-NMR (CDCl$_3$): 156.72, 155.50, 122.84, 121.88, 63.89, 63.73, 57.02, 56.84, 54.61, 50.83, 48.72, 48.60, 48.20, 48.07, 46.61, 46.55, 46.31, 46.09, 44.69, 43.85, 43.65, 43.39, 40.80, 36.57, 36.53, 35.10, 34.97, 34.86, 34.79, 34.69, 31.92, 31.88, 31.45, 27.67, 27.62, 27.57, 27.55, 27.30, 23.41, 23.36, 23.28, 22.97, 7.40.

Preparation of (((((benzene-1,3,5-triyltris(oxy))tris (carbonyl))tris(oxy))tris(propane-3,1-diyl))tris(sulfanediyl))tris(ethane-2,1-diyl)tris(((5-isocyanato-1,3, 3-trimethylcyclohexyl)-methyl)carbamate) (Polyisocyanate 4)

5-Isocyanato-1-(isocyanatomethyl)-1,3,3-trimethylcyclohexane (2.15 mL, 10.15 mmol) and tin(II) 2-ethylhexanoate (0.09 g, 0.011 mmol) were added under nitrogen in a 50 mL round bottomed three necked flask to give a colorless solution. Benzene-1,3,5-triyl tris(3-((2-hydroxyethyl)thio) propyl)tricarbonate (Multi-Alcohol 32, 2.02 g, 3.30 mmol) in ethyl acetate (3 mL) was added dropwise during 5 min. The reaction mixture was stirred for 3 h at 50° C. and then slowly cooled to room temperature under stirring.

$^1$H-NMR (CDCl$_3$): 7.04, 6.99, 4.96, 4.67, 4.37, 4.21, 3.80, 3.66, 3.50, 3.47, 3.38, 3.35, 3.33, 3.25, 3.23, 3.21, 3.06, 3.01, 2.93, 2.90, 2.76, 2.70, 1.85, 1.83, 1.78, 1.72, 1.25-0.80.

$^{13}$C-NMR (CDCl$_3$): 156.71, 155.41, 152.66, 151.44, 121.92, 112.07, 67.55, 63.73, 57.02, 56.83, 54.61, 50.80, 48.68, 48.59, 48.39, 48.20, 48.05, 47.87, 46.59, 46.54, 46.29, 46.07, 44.69, 43.85, 43.63, 43.38, 41.49, 36.65, 36.52, 35.04, 34.93, 34.86, 34.83, 34.69, 34.57, 31.89, 31.86, 31.05, 28.50, 28.41, 28.35, 27.64, 27.59, 27.54, 26.85, 23.38, 23.34, 23.23.

Preparation of bis(3-((2-(((3-(isocyanatomethyl) benzyl)carbamoyl)oxy)ethyl)thio)propyl) 2-((2-(((3-(isocyanatomethyl)benzyl)carbamoyl)oxy)ethyl)thio) succinate (Polyisocyanate 5)

1,3-Bis(isocyanatomethyl)benzene (1.4 mL, 8.94 mmol) and tin(II) 2-ethylhexanoate (0.09 g, 2.90 mmol) were added in a 25 mL round bottomed three necked flask to give a colorless solution. A solution of bis(3-((2-hydroxyethyl) thio)propyl) 2-((2-hydroxyethyl)thio)succinate (Multi-Alcohol 33, 1.25 g, 2.90 mmol) in ethyl acetate (0.28 mL) was added dropwise. The reaction mixture was stirred at 50° C. for 3 h, and then cooled to room temperature under stirring.

$^1$H-NMR (CDCl$_3$): 7.41, 7.38, 7.37, 7.32, 7.28, 7.27, 7.22, 7.16, 4.52, 4.48, 4.29, 4.21, 3.69, 2.93, 2.85, 2.71, 2.60, 2.04, 1.90, 1.71.

Preparation of Microcapsules 19 and 20 of the Present Invention with Cleavable Polyisocyanates Comprising Cleavable Multi-Alcohols of Formula (I)

Preparation of Microcapsule 19 from Polyisocyanate 4

Polyisocyanate 4 (4.64 g) was mixed with perfume oil (Perfume 1, 20.01 g) in a 150 mL beaker to give a yellow solution. This mixture was stirred for 5 min. A solution of PVOH 18-88 (Origin, Aldrich, Switzerland) in water (1 wt %, 46.31 g) was added to the mixture. An emulsion was prepared with an Ultra Turrax (S25N 10G) by stirring the reaction mixture at 17,500 rpm for 3 min. The droplet size was controlled by optical microscopy (pH=4.79). The reaction mixture was injected in a 250 mL reactor and stirred at 350 rpm at room temperature for 1 h. Then, the temperature was increased to 70° C. over the course of 1 h, and finally stirred at 70° C. at 350 rpm for 2 h (pH=5.68). The pH was adjusted to 8.8 with a sodium hydroxide solution.

Preparation of Microcapsule 20 from Polyisocyanate 3

Microcapsule 20 was prepared according to protocol described for Microcapsule 19 from Polyisocyanate 3 (5.32 g) in the perfume oil.

Example 5

Perfume Leakage in a Fabric Softener Application

The storage stability of the capsules was evaluated in a fabric softener formulation (see composition in Table 2). Capsule dispersions were diluted in the fabric softener (29.73 g) to obtain a final concentration of Perfume 2 of 0.20 wt %. The softener was stored for up to one month at 37° C. The amount of perfume leaked out of the capsules was then measured by solvent extraction with isooctane (10 mL) under stirring.

TABLE 2

Fabric softener composition:

| Product | Origin | Wt % |
|---|---|---|
| Stepantex VL 90A | Stepan | 8.88 |
| Calcium Chloride Sol. 10% | | 0.36 |
| Proxel GXL | Avecia | 0.04 |
| Water | | 90.72 |
| TOTAL | | 100 |

Protocol for the Stability Assessment

A fabric softener base comprising microcapsules (2 g) was introduced into a 20 mL vial. The sample was diluted with water (2 mL) to decrease the viscosity using a Socorex 10 mL bottle top dispenser. The samples were shaken for 5 min using the Turbulat Shaker set at 40 rpm. Isooctane, containing 1,4-dibromobenzene as an internal standard at a precisely known concentration around 90 ng/μL, was added to the vial (10 mL). The samples were shaken for 45 min at 40 rpm to extract the free perfume and then centrifuged for 10 min at 3.0 G to separate the two phases. The solvent phase was recovered and dried on $MgSO_4$ for GC analysis.

TABLE 3

Perfume leakage from microcapsules in a fabric softener after storage at 37° C. for 3 days:

| Microcapsule | Leakage (%) |
|---|---|
| 5 | 23.0 |
| 6 | 19.8 |
| 9 | 10.0 |
| 10 | 10.0 |
| 11 | 10.0 |

Microcapsules according to the invention show therefore a good stability in a fabric softener.

Example 6

Liquid Detergent Composition

Microcapsules 1-20 of the present invention are dispersed in a liquid detergent base described in Table 4 to obtain a concentration of encapsulated perfume oil at 0.22%.

TABLE 4

Liquid detergent composition:

| Ingredients | Concentration [wt %] |
|---|---|
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene glycol | 11 |
| Citric acid | 6.5 |
| Potassium hydroxide | 9.5 |
| Protease | 0.2 |
| Amylase | 0.2 |
| Mannanase | 0.2 |
| Acrylates/Steareth-20 Methacrylate structuring Crosspolymer[4] | 6 |
| Deionized water | 27.4 |

[1] Hostapur SAS 60; Origin: Clariant
[2] Edenor K 12-18; Origin: Cognis
[3] Genapol LA 070; Origin: Clariant
[4] Aculyn 88; Origin: Dow Chemical Example 7

Rinse-Off Conditioner

Microcapsules 1-20 of the present invention are dispersed in a rinse-off conditioner base described in table 5 to obtain a concentration of encapsulated perfume oil at 0.5%.

TABLE 5

Rinse-off conditioner composition:

| | Ingredients | Concentration [wt %] |
|---|---|---|
| A | Deionized water | 81.8 |
| | Behentrimonium chloride [1] | 2.5 |
| | Hydroxyethylcellulose [2] | 1.5 |
| B | Cetearyl alcohol [3] | 4 |
| | Glyceryl stearate (and) PEG-100 stearate [4] | 2 |
| | Behentrimonium methosulfate (and) Cetyl alcohol (and) Butylene glycol [5] | 4 |
| | Ethoxy (20) stearyl alcohol [6] | 1 |
| C | Amodimethicone (and) Trideceth-12 (and) Cetrimonium chloride [7] | 3 |
| | Chlorhexidine digluconate [8] 20% aqueous solution | 0.2 |
| D | Citric acid 10% aqueous sol. till pH 3.5-4 | q.s. |
| | TOTAL: | 100 |

[1] Genamin KDM P, Clariant
[2] Tylose H10 Y G4, Shin Etsu
[3] Lanette O, BASF
[4] Arlacel 165-FP-MBAL-PA-(RB), Croda
[5] Incroquat Behenyl TMS-50-MBAL-PA-(MH) HA4112, Croda
[6] SP Brij S20 MBAL-PA(RB), Croda
[7] Xiameter DC MEM-0949 Emulsion, Dow Corning
[8] Alfa Aesar

Example 8

Shampoo Composition

Microcapsules 1-20 of the present invention are weighed and mixed in a shampoo composition to add the equivalent of 0.2% perfume.

TABLE 6

Shampoo composition:

|   | Ingredients | Concentration [wt %] |
|---|---|---|
| A | Water deionized | 44.4 |
|   | Polyquaternium-10 [1] | 0.3 |
|   | Glycerin 85% [2] | 1 |
|   | DMDM Hydantoin [3] | 0.2 |
| B | Sodium Laureth Sulfate [4] | 28 |
|   | Cocamidopropyl Betaine [5] | 3.2 |
|   | Disodium Cocoamphodiacetate [6] | 4 |
|   | Ethoxy (20) Stearyl Alcohol [6] | 1 |
| C | Sodium Laureth Sulfate [4] | 3 |
|   | Glyceryl Laureate [7] | 0.2 |
| D | Water deionized | 1 |
|   | Sodium Methylparaben [8] | 0.1 |
| E | Sodium Chloride 10% aqueous sol. | 15 |
|   | Citric acid 10% aqueous sol. till pH 5.5-6 | q.s. |
|   | Perfume | 0.5 |
|   | TOTAL: | 100 |

[1] Ucare Polymer JR-400, Noveon
[2] Schweizerhall
[3] Glydant, Lonza
[4] Texapon NSO IS, Cognis
[5] Tego Betain F 50, Evonik
[6] Amphotensid GB 2009, Zschimmer & Schwarz
[7] Monomuls 90 L-12, Gruenau
[8] Nipagin Monosodium, NIPA

Example 9

Antiperspirant Roll-on Emulsion Composition

Microcapsules 1-20 of the present invention are weighed and mixed in antiperspirant roll-on emulsion composition to add the equivalent of 0.2% perfume.

TABLE 7

Antiperspirant roll-on emulsion composition:

| Ingredient | Amount (wt %) |
|---|---|
| Steareth-2 [1] (Part A) | 3.25 |
| Steareth-21 [2] (Part A) | 0.75 |
| PPG-15 Stearyl ether [3] (Part A) | 4 |
| Deionized water (Part B) | 51 |
| Aluminum chlorohydrate 50% aqueous solution [4] (Part C) | 40 |
| Fragrance (Part D) | 1 |

[1] BRIJ 72; origin: ICI
[2] BRIJ 721; origin: ICI
[3] ARLAMOL E; origin: UNIQEMA-CRODA
[4] LOCRON L; origin: CLARIAN Part A and B are heated separately to 75° C.; Part A is added to Part B under stirring and the mixture is homogenized for 10 min. Then, the mixture is cooled under stirring; and Part C is slowly added when the mixture reached 45° C. and Part D when the mixture reached at 35° C. while stirring. Then the mixture is cooled to room temperature.

Example 10

Shower-Gel Composition

Microcapsules 1-20 of the present invention are weighed and mixed in the following composition to add the equivalent of 0.2% perfume.

TABLE 8

Shower gel composition:

| Ingredients | Amount (% wt) | Function |
|---|---|---|
| Deionized water | 49.350 | Solvent |
| Tetrasodium EDTA [1] | 0.050 | Chelating agent |
| Acrylates copolymer [2] | 6.000 | Thickener |
| Sodium C12-C15 pareth sulfate [3] | 35.000 | Surfactant |
| Sodium hydroxide 20% aqueous solution | 1.000 | pH adjuster |
| Cocamidopropyl betaine [4] | 8.000 | Surfactant |
| Methylchloroisothiazolinone and Methylisothiazolinone [5] | 0.100 | Preservative |
| Citric acid (40%) | 0.500 | pH adjuster |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS

The invention claimed is:

1. A process for a preparation of a core-shell microcapsule slurry comprising the following steps:
   a) adding at least one polyfunctional monomer in a hydrophobic material to form an oil phase;
   b) preparing a dispersing phase, wherein the dispersing phase is not miscible with the oil phase;
   c) adding the oil phase into the dispersing phase to form a two-phase dispersion;
   d) optionally, adding a reactant to the dispersion obtained in step c); and
   e) performing a curing step to form core-shell microcapsules in the form of a slurry,
   wherein a stabilizer is added in step a) and/or step b),
   wherein at least one cleavable multi-alcohol is added in step a) and/or in step b) and/or in step c) and/or in step d),
   wherein the cleavable multi-alcohol has the following formula (I)

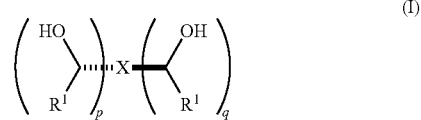

wherein each $R^1$ is independently H or $CH_2OH$ and wherein p and q are integers varying between 1 and 3,
wherein X is a $C_2$ to $C_{30}$ hydrocarbon group, optionally comprising one to ten heteroatoms, selected from the group consisting of O, S and N to form ether, ester, carboxylic acid, aldehyde, ketone, alcohol, thiol, disulfide, thioether, thioester, carbamate, amide, oxime, imine, amine or nitrile functional groups;
wherein the cleavable multi-alcohol is not trimethylol propane; and
wherein the core-shell microcapsules comprise a reaction product between the polyfunctional monomer and the cleavable multi-alcohol.

2. The process according to claim 1, wherein X is a compound selected from the group consisting of disulfides, oxazolidines, imines, 1,4-addition products, carbonates and aryl ketone derivatives.

3. The process according to claim 1, wherein X is selected from the group consisting of
(a) 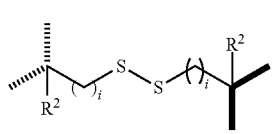
(b) 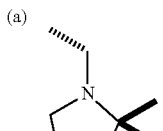
(c) 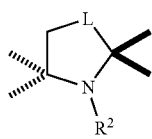
(d) 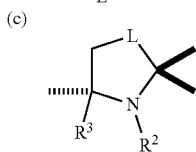
(e) 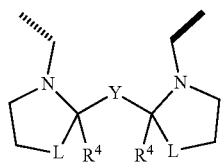
(f) 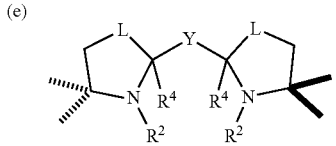
(g) 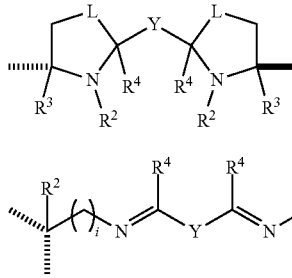
(h) 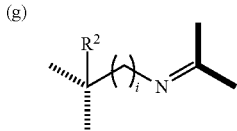
(i) 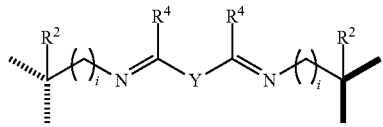
(j) 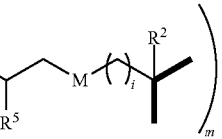
(k) 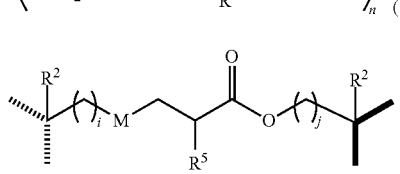
(l) 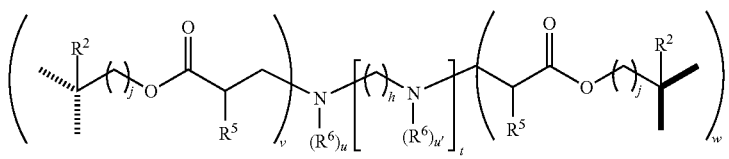
(m) 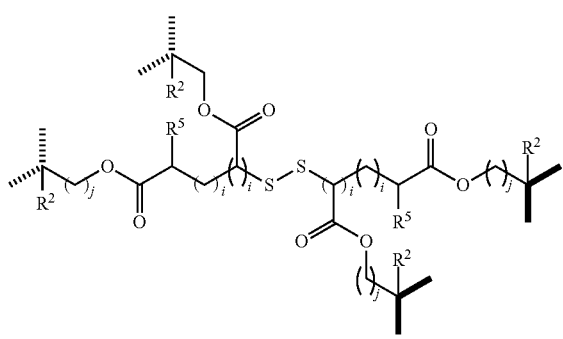
(n) 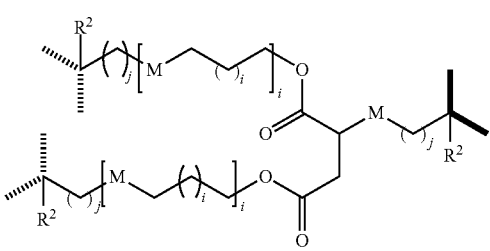

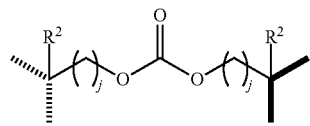

(o)

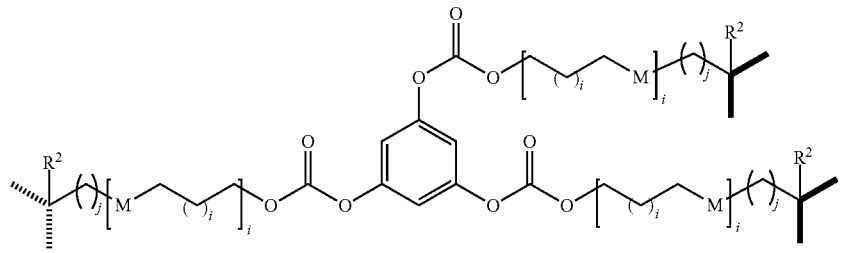

(p)

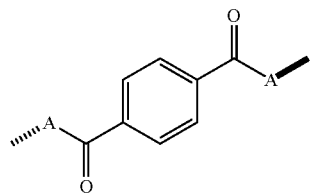

(q)

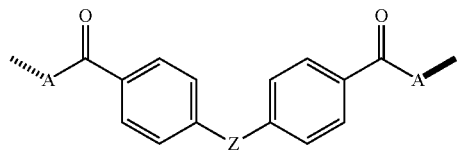

(r)

with L being a O or a S atom or a NH group, M being a S atom or a NR$^6$ group, Y being a CH$_2$, a CH$_2$—CH$_2$ or a phenyl group, Z being a O(CH$_2$)$_x$O or a (CH$_2$)$_x$ group with x being an integer varying between 1 and 4, and A being a COOCH$_2$(CR$^2$R$^2$)$_i$, CHR$_2$OCH$_2$(CR$_2$R$_2$); or (CR$^2$R$^2$)(CHR$^2$)$_x$ group, with each R$^2$ being independently a H, CH$_3$, CH$_2$CH$_3$, CH$_2$OH or CH$_2$CH$_2$OH group and each R$^3$ being independently a CH$_3$ or CH$_2$CH$_3$ group, with R$^4$ being either H or CH$_3$ or, if Y is not phenyl group, then two R$^4$ taken together may represent a CH$_2$ or a CH$_2$—CH$_2$ group, with R$^5$ being either H or CH$_3$, with R$^6$ being either H, a C$_1$-C$_6$ alkyl group or a CH$_2$—CH$_2$—(CH$_2$)$_j$—OH group, if t=1 two R$^6$ taken together might form a CH$_2$—CH$_2$—(CH$_2$)$_i$ group, with h being an integer varying between 1 and 6, each i being individually of each other 0 or 1, each j being individually of each other an integer varying between 0 and 2, and with k and l being integers varying between 0 and 2, and m and n being 1 or 2, with the proviso that k+l+m+n=4, with t, u and u' being 0 or 1, v and w being 1 or 2, and with the proviso that u+v+w=3 (if t=0) or u+u'+v+w=4 (if t=1), and wherein the hatched and the bold lines are either linked to a hydrogen atom or indicate the bond between said X and the (CHR$^1$OH)$_p$ (hatched line) or (CHR$^1$OH)$_q$ (bold line) groups of the multi-alcohol of formula (I), with the proviso that at least one hatched and at least one bold line of X are linked to a CHR$^1$OH group.

4. The process according to claim 1, wherein the cleavable multi-alcohol is a compound selected from the group consisting of:

disulfides selected from the group consisting of 2,2'-disulfanediylbis(ethan-1-ol), 2,2'-disulfanediylbis(propane-1,3-diol), 3-(2,3-dihydroxypropyldisulfanyl)propane-1,2-diol, 2,2'-(disulfanediylbis(methylene))bis(2-methylpropane-1,3-diol), 2,2'-(disulfanediylbis(methylene))bis(2-ethylpropane-1,3-diol), bis(3-hydroxy-2-(hydroxymethyl)-2-methylpropyl) 3,3'-disulfanediyldipropionate, and tetrakis(2-hydroxyethyl) 2,2'-disulfanediyldisuccinate, oxazolidines selected from the group consisting of (3-(2-hydroxyethyl)oxazolidine-2,2-diyl)dimethanol, oxazolidine-2,2,4-triyltrimethanol, 2,2'-(ethane-1,2-diylbis(2-methyloxazolidine-2,3-diyl))bis(ethan-1-ol), (ethane-1,2-diylbis(2-methyloxazolidine-2,4,4-triyl))tetramethanol, 2,2'-(1,4-phenylenebis(oxazolidine-2,3-diyl))bis(ethan-1-ol), 2,2'-(furan-2,5-diylbis(oxazolidine-2,3-diyl))bis(ethan-1-ol), 2,2'-(cyclohexane-1,4-diylbis(oxazolidine-2,3-diyl))bis(ethan-1-ol), 2,2'-(1,9-dioxa-4,12-diazadispiro[4.2.4$^8$.2$^5$] tetradecane-4,12-diyl)bis(ethan-1-ol), (1,4-phenylenebis(oxazolidine-2,4,4-triyl))tetramethanol, (1,9-dioxa-4,12-diazadispiro[4.2.4$^8$.2$^5$]tetradecane-3,3,11,11-tetrayl)tetramethanol, (1,9-dioxa-4,12-diazadispiro[4.2.4$^8$.2$^5$]tetradecane-3,11-diyl)dimethanol, (3,11-diethyl-1,9-dioxa-4,12-diazadispiro[4.2.4$^8$.2$^5$]tetradecane-3,11-diyl)dimethanol, (1,4-phenylenebis(4-ethyloxazolidine-2,4-diyl))dimethanol, (3,11-diethyl-1,9-dioxa-4,12-diazadispiro[4.2.4$^8$.2$^5$]tetradecane-3,11-diyl)dimethanol, and 2,2'-(3,11-bis(hydroxymethyl)-1,9-dioxa-4,12-diazadispiro[4.2.4$^8$.2$^5$]tetradecane-4, 12-diyl)bis(ethan-1-ol), imines and Schiff bases selected from the group consisting of 2,2'-((1,4-phenylenebis(methanylylidene))bis(azanylylidene))bis(propane-1,3-diol), and 2,2'-((furan-2,5-diylbis(methanylylidene))bis(azanylylidene))bis(propane-1,3-diol), 1,4-Addition products selected from the group consisting of 2-hydroxyethyl 3-((2-hydroxyethyl)thio)propanoate, 3-hydroxy-2-(hydroxymethyl)-2-methylpropyl 3-((3-hydroxy-2-(hydroxymethyl)-2-methylpropyl)thio)-2-methylpropanoate, 3-hydroxy-2-(hydroxymethyl)-2-methylpropyl(S)-3-((2,3-dihydroxypropyl)thio) propanoate, 2-ethyl-2-(((3-((2-hydroxyethyl)thio)propanoyl)oxy)methyl) propane-1,3-diyl bis(3-((2-hydroxyethyl)thio) propanoate), 4-hydroxybutyl 3-((1,3-dihydroxypropan-2-yl)amino)propanoate, bis(2-hydroxyethyl) 3,3'-(butylazanediyl)dipropionate, bis (2-hydroxyethyl) 3,3'-((4-hydroxybutyl)azanediyl) dipropionate, bis(2-hydroxyethyl) 3,3'-(piperazine-1,4-diyl)dipropionate, tetrakis(2-hydroxyethyl) 3,3',3",3'-(propane-1,3-diylbis(azanetriyl))tetrapropionate, and bis(3-((2-hydroxyethyl)thio)propyl) 2-((2-hydroxyethyl)thio)succinate, carbonates selected from the group consisting of bis(2,3-dihydroxypropyl) carbonate, bis(3-hydroxy-2-(hydroxymethyl)-2-methylpropyl) carbonate, and benzene-1,3,5-triyl tris(3-((2-hydroxyethyl)thio) propyl) tricarbonate, aryl ketone derivatives selected from the group consisting of bis(2-hydroxyethyl) 2,2'-(methylenebis(4,1-phenylene))bis(2-oxoacetate), bis(2,2-bis(hydroxymethyl) butyl) 2,2'-(methylenebis(4,1-phenylene))bis(2-oxoacetate), bis(2-hydroxyethyl) 2,2'-(ethane-1,2-diylbis(4,1-phenylene))bis(2-oxoacetate), bis(3-hydroxy-2-(hydroxymethyl)-2-methylpropyl) 2,2'-(1,4-phenylene) bis(2-oxoacetate), and 1,1'-(1,4-phenylene)bis(5-hydroxypentan-1-one), and mixtures thereof.

5. The process according to claim 1, wherein the polyfunctional monomer is selected from the group consisting of at least one polyisocyanate, polyanhydride, poly acyl chloride, polyepoxide, polyacrylate monomers, polymethacrylate and polyalkoxysilane, and mixtures thereof.

6. The process according to claim 1, wherein the reactant is selected from the group consisting of nitrogen nucleophile, sulfur nucleophile, enol carbon nucleophile, oxygen nucleophile, phosphor nucleophile and mixtures thereof.

7. The process according to claim 6, wherein the reactant is selected from the group consisting of xylylene diamine, 1,2-diaminocyclohexane, 1,4-diaminocyclohexane, L-lysine, L-Lysine ethyl ester, O,O'-bis(2-aminopropyl)polypropylene glycol-block-polyethylene glycol-block-polypropylene glycol, ethylene diamine, 1,3-diamino-2-hydroxypropane, diethylene triamine, spermine, spermidine, cystamine, cystine, cystine dialkyl ester, aminoguanidine bicarbonate, N,N'-diethylethylenediamine, polyamidoamine (PAMAM), chitosan, 3-aminopropyltriethoxysilane, L-arginine, 1,3-diaminopropane, N-ethylguanidine sulfate, 1,6-diaminohexane, guanidine salts, N,N,N',N'-tetrakis(3-aminopropyl)-1,4-butanediamine, guanazole, 2-amino-1,3-propanediol, ethanolamine tris(2-aminoethyl) mine, tris(3-aminopropyl)amine, tris[2-(methylamino)ethyl]amine, 1-(2-Aminoethyl) piperazine, triethylenetetramine, triethanolamine, phthalic acid dipotassium salt, succinic acid disodium salt, dithiothreitol and mixtures thereof.

8. The process according to claim 1, wherein the stabilizer is selected from the group consisting of gum Arabic, modified starch, polyvinyl alcohol, polyvinylpyrrolidone, carboxymethylcellulose, anionic polysaccharides, acrylamide copolymer, inorganic particles, proteins and mixtures thereof.

9. The process according to claim 1, wherein the hydrophobic material is a perfume.

10. The process according to claim 1, wherein p and q are either 1 or 2.

11. The process according to claim 3, with L being a O atom and M being a S atom.

* * * * *